(12) United States Patent
Monaghan

(10) Patent No.: US 6,350,735 B1
(45) Date of Patent: Feb. 26, 2002

(54) PURINE DERIVATIVES

(75) Inventor: Sandra Marina Monaghan, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/688,624

(22) Filed: Oct. 16, 2000

(30) Foreign Application Priority Data

Oct. 14, 1999 (GB) .............................................. 9924363

(51) Int. Cl.[7] .......................... A61K 31/70; C07H 19/00
(52) U.S. Cl. ............................ 514/46; 514/45; 514/47; 536/27.2; 536/27.21; 536/27.3; 536/27.6
(58) Field of Search ............................ 536/27.2, 27.21, 536/27.3, 27.6; 514/45, 46, 47

(56) References Cited

FOREIGN PATENT DOCUMENTS

| WO | 9111172 | 8/1991 | ............ A61K/9/00 |
|----|---------|--------|------------------------|
| WO | 9402518 | 2/1994 | ............ C08B/37/16 |
| WO | 9855148 | 12/1998 | ........... A61K/47/48 |

OTHER PUBLICATIONS

J. Amer. Chem. Soc., vol. 80, pp. 5168–5173, 1958.*
J. Pharm. Sci., vol. 53, pp. 73, 1964.*
J. Pharm Sci., vol. 66, pp. 1–19, 1977.*
J. Prakt. Chem., vol. 321, pp. 248, 1992.*
J. Med. Chem., 35, p. 248, 1992.

* cited by examiner

*Primary Examiner*—James O. Wilson
(74) *Attorney, Agent, or Firm*—Peter C. Richardson; Paul H. Ginsburg; Raymond M. Speer

(57) ABSTRACT

The present invention relates to compounds of the formula

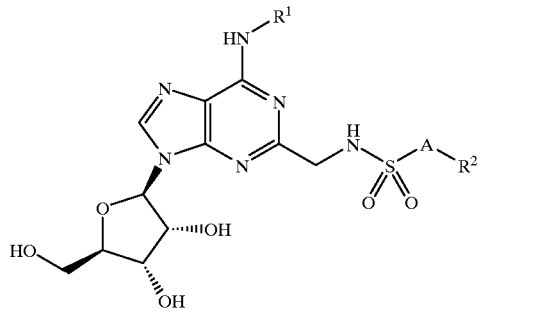

(I)

and pharmaceutically acceptable salts and solvates thereof, to processes for the preparation of, intermediates used in the preparation of, and compositions containing such compounds and the uses of such compounds as adenosine A2a receptor agonists.

32 Claims, No Drawings

PURINE DERIVATIVES

REFERENCE TO COPENDING APPLICATIONS

This application is a continuation of copending prior filed international application designating the U.S. Ser. No. PCT/IB00/01444 filed Oct. 6, 2000, the benefit of the filing date of which is claimed, and which is incorporated herein by reference in its entirety; and corresponds to copending prior filed foreign application Great Britain Serial No. 9924363.6 filed Oct. 14, 1999, the benefit of the filing date of which is claimed, and which is incorporated herein by reference in its entirety.

This invention relates to purine derivatives. More particularly, this invention relates to N-[(purin-2-yl)methyl] sulphonamide derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2^-$), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemoattractant that recruits additional neutrophils to the inflammatory focus, whereas released $O_2^-$ and HNE adversely affect the pulmonary extracellular matrix. The A2 receptor subtype mediating many of these responses ($O_2^-$ and $LTB_4$/HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)—induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylon* gastritis, non-*Heliobacter pylon* gastritis, non-steroidal anti-inflammatory drug-induced damage to the gastro-intestinal tract or a psychotic disorder, or for wound healing.

Accordingly, the present invention provides a compound of the formula:

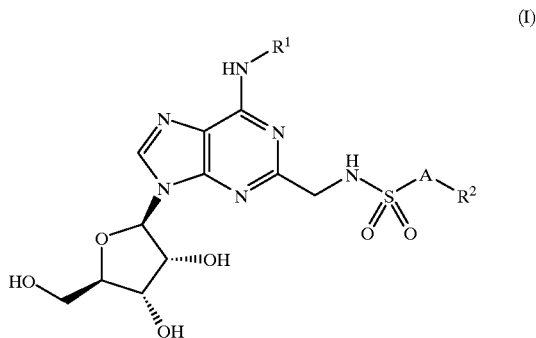

(I)

or a pharmaceutically acceptable salt or solvate thereof, wherein $R^1$ is hydrogen or $C_1$–$C_6$ alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

A is a bond or $C_1$–$C_3$ alkylene;

$R^2$ is (i) hydrogen, $C_1$–$C_6$ alkyl, $C_3$–$C_7$ cycloalkyl, phenyl or naphthyl, said $C_3$–$C_7$ cycloalkyl, phenyl or naphthyl being optionally substituted by $C_1$–$C_6$ alkyl, phenyl, $C_1$–$C_6$ alkoxy-($C_1$–$C_6$)-alkyl, $R^3R^3N$—($C_1$–$C_6$)-alkyl, fluoro-($C_1$–$C_6$)-alkyl fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$, —$NR^3R^3$, —$SO_2NR^3R^3$, —$CONR^3R^3$, —$NR^3COR^4$ or —$NR^3SO_2R^4$, with the proviso that $R^2$ is not hydrogen when A is a bond, or (ii) when A is $C_2$–$C_3$ alkylene, —$NR^7R^8$, —$OR^3$, —$COOR^3$, —$OCOR^4$, —$SO_2R^4$, —$CN$, —$SO_2N R^3R^3$, —$NR^3COR^4$ or —$CON\ R^3R^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^3R^3N$—($C_1$–$C_6$)-alkyl, fluoro-($C_1$–$C_6$)-alkyl, fluoro-($C_1$–$C_6$)-alkoxy, fluoro-($C_2$–$C_5$)-alkanoyl, halo, cyano, —$OR^5$, $R^6$, —$COR^5$, —$NR^5R^5$, —$COOR^5$, $S(O)_mR^6$, —$SO_2NR^5R^5$, —$CONR^5R^5$, —$NR^5SO_2R^6$ or —$NR^5COR^6$ and optionally N-substituted by $C_1$–$C_6$ alkoxy-($C_1$–$C_6$)-alkyl, $R^3R^3N$—($C_2$–$C_6$)-alkyl, fluoro-($C_1$–$C_6$)-alkyl, fluoro-$C_2$–$C_5$)-alkanoyl, $R^6$, —$COR^5$, —$COOR^5$, —$S(O)_mR^6$, —$SO_2NR^5R^5$ or —$CONR^5R^5$;

$R^3$ is H, $C_1$–$C_6$ alkyl, $C_3$–$C_7$ cycloalkyl or phenyl;

$R^4$ is $C_1$–$C_6$ alkyl, $C_3$–$C_7$ cycloalkyl or phenyl;

$R^5$ is H, $C_{1-C6}$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

either, $R^7$ and $R^8$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^3R^3N$—($C_1$–$C_6$)-alkyl, fluoro-($C_1$–$C_6$)-alkyl, —$CONR^3R^3$, —$COOR^3$ or $C_2$–$C_5$ alkanoyl, and optionally substituted on a ring carbon atom not adjacent to a ring nitrogen atom by fluoro-($C_1$–$C_6$)-alkoxy, halo, —$OR^3$, cyano, —$S(O)_mR^4$, —$NR^3R^3$, —$SO_2NR^3R^3$, —$NR^3COR^4$ or —$NR^3SO_2R^4$, and said piperazin-1-yl and homopiperazin-1-yl being optionally substituted on the ring nitrogen atom not attached to A by $C_1$–$C_6$ alkyl, phenyl, $C_1$–$C_6$ alkoxy-($C_2$–$C_6$)-alkyl, $R^3R^3N$—($C_2$–$C_6$)-alkyl, fluoro-($C_1$–$C_6$)-alkyl, $C_2$–$C_5$ alkanoyl, —$COOR^4$, $C_3$–$C_8$ cycloalkyl, —$SO_2R^4$, —$SO_2NR^3R^3$ or —$CONR^3R^3$, or, $R^7$ is H, $C_1$–$C_6$ alkyl, $C_3$–$C_8$ cycloalkyl, phenyl or benzyl and $R^8$ is H, $C_1$–$C_6$ alkyl, $C_3$–$C_8$ cycloalkyl, phenyl, benzyl, fluoro-($C_1$–$C_6$)-alkyl, —$CONR^3R^3$, —$COOR^4$, $C_2$–$C_5$ alkanoyl or —$SO_2NR^3R^3$;

m is 0, 1 or 2; and

"het", used in the definitions of $R^5$ and $R^6$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo.

In the above definitions, halo means fluoro, chloro, bromo or iodo and alkyl, alkylene, alkanoyl and alkoxy groups containing the requisite number of carbon atoms can be unbranched or branched chain. The heterocycle as defined in $R^2$, part (iii), above may be aromatic or fully or partially saturated. The expression 'C-linked' used in the definition of $R^2$ and "het" means that the group is linked to the adjacent atom by a ring carbon atom. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19 (1977).

The pharmaceutically acceptable solvates of the compounds of the formula (I) include the hydrates thereof.

Also included within the present scope of the compounds of the formula (I) are polymorphs thereof.

A compound of the formula (I) may contain one or more additional asymmetric carbon atoms and therefore exist in two or more stereoisomeric forms. The present invention includes the individual stereoisomers of the compounds of the formula (I) together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$ alkyl optionally substituted by 1 or 2 substituents each independently selected from phenyl and naphthyl.

Preferably, $R^1$ is $C_1$–$C_6$ alkyl substituted by 1 or 2 substituents each independently selected from phenyl and naphthyl.

Preferably, $R^1$ is $C_1$–$C_4$ alkyl substituted by 1 or 2 substituents each independently selected from phenyl and naphthyl.

Preferably, $R^1$ is $C_1$–$C_2$ alkyl substituted by 1 or 2 substituents each independently selected from phenyl and naphthyl.

Preferably, $R^1$ is phenylethyl, diphenylethyl or naphthylmethyl.

Preferably, $R^1$ is 2-phenylethyl, 2,2-diphenylethyl or 1-naphthylmethyl.

Preferably, A is a bond.

Preferably, A is $C_1$–$C_3$ alkylene.

Preferably, A is $C_2$–$C_3$ alkylene.

Preferably, A is $C_2$ alkylene.

Preferably, A is —$CH_2CH_2$—.

Preferably, $R^2$ is $C_1$–$C_6$ alkyl, phenyl or $NR^7R^8$.

Preferably, $R^2$ is 2-methylprop-1-yl, phenyl or $NR^7R^8$.

Preferably, —A—$R^2$ is 2-methylprop-1-yl, phenyl or —$CH_2CH_2NR^7R^8$.

Preferably, $R^7$ is $C_1$–$C_6$ alkyl.

Preferably, $R^7$ is $C_1$–$C_3$ alkyl.

Preferably, $R^7$ is propyl.

Preferably, $R^7$ is prop-2-yl.

Preferably, $R^8$ is $C_3$–$C_8$ cycloalkyl.

Preferably, $R^8$ is $C_3$–$C_6$ cycloalkyl.

Preferably, $R^8$ is cyclopentyl.

Preferred heterocycles included in the definition of $R^2$, part (iii) are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl, quinoxalinyl, 1,2-dihydroisoquinolinyl, 3,4-dihydroisoquinolinyl, 1,2,3,4-tetrahydroisoquinolinyl, azetidinyl, pyrrolidinyl, piperidinyl, tetrahydropyranyl, tetrahydrothiopyranyl, morpholinyl and piperazinyl.

Preferred examples of compounds of the formula (I) include those of the Examples section hereafter, including any pharmaceutically acceptable salts thereof.

The compounds of the formula (I) can be prepared by conventional routes such as by the procedures described in the general methods presented below or by the specific methods described in the Examples section, or by similar methods thereto. The present invention also encompasses these processes for preparing the compounds of formula (I), in addition to any novel intermediates used therein. In the general methods described, $R^1$, $R^2$ and A are as previously defined unless otherwise stated.

All the compounds of formula (I) may be prepared by the deprotection of a compound of formula

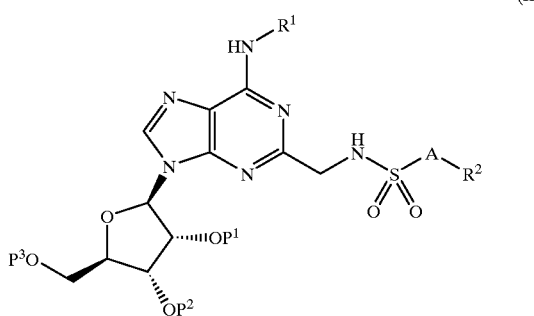

(II)

wherein $P^1$, $P^2$ and $P^3$ represent suitable protecting groups which may be the same or different or $P^1$ and $P^2$ optionally form part of the same protecting group. Examples of suitable protecting groups will be apparent to the skilled person [see for instance 'Protecting Groups in Organic Synthesis (Second Edition)', Theodora W. Green and Peter G. M. Wuts, John Wiley and Sons, 1991]. Preferred individual protecting groups are silyl (substituted with three groups independently selected from aryl and alkyl), alkanoyl and aroyl. A preferred protecting group where $P^1$ and $P^2$ form part of the same protecting group is where $P^1$ and $P^2$ taken together are $C_1$–$C_6$ alkylene. Particularly preferred individual protecting groups are acetyl and benzoyl. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$, $P^2$ and $P^3$ are each acetyl, the protecting groups may be removed by treating a solution of the compound of formula (II) in a suitable solvent, such as a mixture of water and methanol, with a base such as sodium carbonate, typically at room temperature.

The protecting groups $P^1$, $P^2$ and $P^3$ may be removed together in a single step or sequentially, in any order. Alternatively, any two of the protecting groups $P^1$, $P^2$ and $P^3$ may be removed together in a single step and the remaining group may be removed in a separate step, in either order.

The compounds of formula (II) may be prepared according to the routes shown in Schemes 1 and 2, in which X is a leaving group, preferably chloro and $P^1$, $P^2$ and $P^3$ are as defined above.

Scheme 1

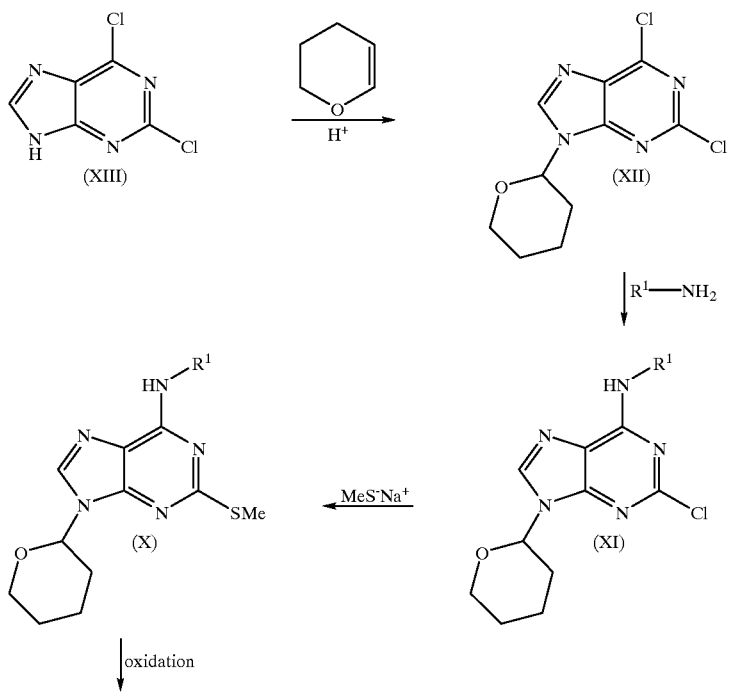

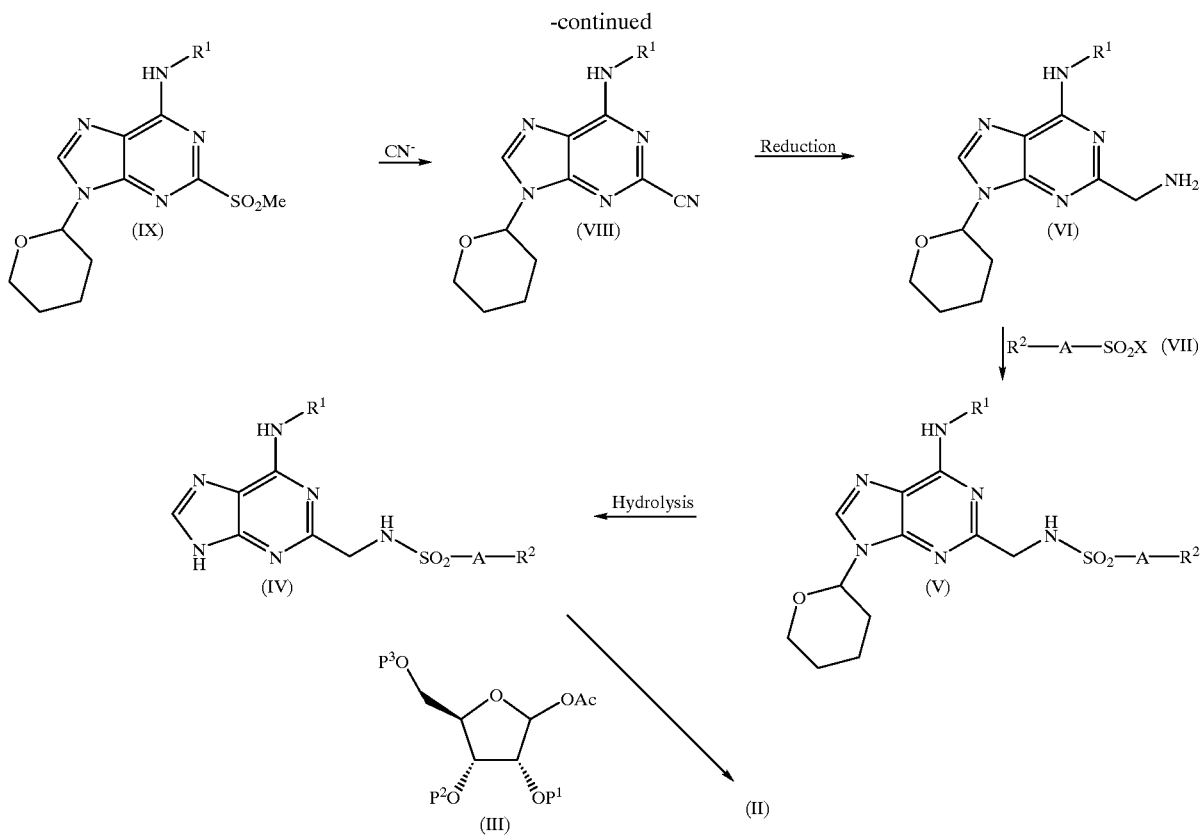

In Scheme 1, compounds of the formula (II) may be prepared by the reaction of a compound of the formula (III) with a compound of the formula (IV) according to known methods. In a typical procedure, the compound of the formula (III) is heated with N,O-bis(trimethylacetamide) in an inert solvent such as 1,1,1-trichloroethane, the solvent is removed and a solution of the residue, in a suitable solvent such as toluene, is heated, preferably under reflux, with the compound of the formula (IV) and trimethylsilyltriflate. Compounds of the formula (IV) may be prepared by the hydrolysis of a compound of the formula (V). Typically, the compound of the formula (V) is dissolved in a suitable solvent, such as ethanol, and treated with an acid such as hydrochloric acid. The reaction is preferably performed from 0 to 100° C., most preferably from 20 to 50° C. Compounds of the formula (V) may be prepared by the sulphonylation of a compound of the formula (VI) with a compound of the formula (VII). In a typical procedure, a solution of the compound of the formula (VI) in a suitable inert solvent such as dichloromethane is treated with the compound of the formula (VII). An acid acceptor such as triethylamine may optionally be added. Compounds of the formula (VI) may be prepared by the reduction of a compound of the formula (VII). The reduction may be carried out with any suitable hydride reducing agent or by hydrogenation. In a typical procedure, a solution of the compound of the formula (VIII) in a suitable solvent such as ethanol is saturated with ammonia gas, treated with an appropriate hydrogenation catalyst such as Pearlmann's catalyst and pressurised with hydrogen, preferably to about 414 kPa (60 psi). Compounds of the formula (VIII) may be prepared by reacting a compound of the formula (IX) with a source of cyanide anion such as potassium cyanide. The reaction is typically carried out in a solvent such as N,N-dimethylformamide at an elevated temperature. Compounds of the formula (IX) may be prepared by the oxidation of a compound of the formula (X). In a typical procedure, an aqueous solution of potassium peroxymonosulphate is added to a solution of the compound of the formula (X) and sodium hydrogencarbonate in a suitable solvent, such as a mixture of water and acetone. Compounds of the formula (X) may be prepared by the displacement of chloride in a compound of the formula (XI) with thiomethoxide. Typically, the reaction is carried out in a polar solvent such as N,N-dimethylformamide, at elevated temperatures and under an atmosphere of nitrogen. Thiomethoxide is used as an alkali metal salt such as sodium thiomethoxide. Compounds of the formula (XI) may be prepared by the reaction of a compound of the formula (XII) with an appropriate primary amine. Typically, a solution of the dichloropurine (XII) in a solvent such as isopropyl alcohol is treated with the amine and heated under reflux. An additional acid acceptor such as diphenylethylamine may optionally be added. Compound (XII) may be prepared by the reaction of 2,6-dichloro-9H-purine (XIII) with dihydropyran in a suitable solvent such as ethyl acetate and in the presence of an acid catalyst such as 4-toluenesulphonic acid, usually at an elevated temperature.

Scheme 2

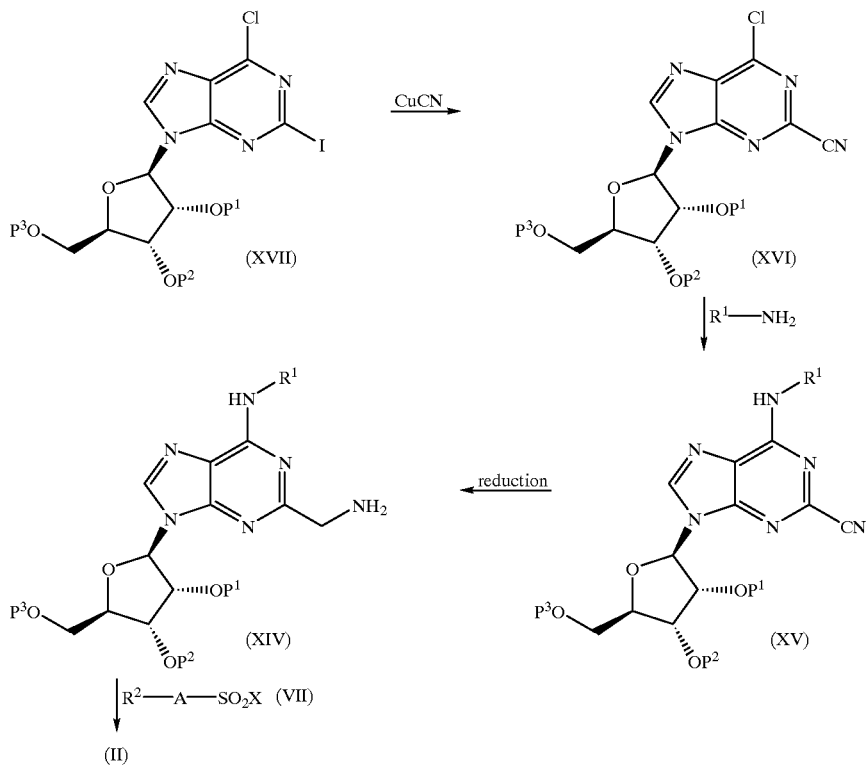

In Scheme 2, compounds of the formula (II) may be prepared by the sulphonylation of a compound of the formula (XIV) with a compound of the formula (VII). In a typical procedure, a solution of the compound of the formula (XIV) in a suitable inert solvent such as dichloromethane is treated with the compound of the formula (VII). An acid acceptor such as triethylamine may be optionally added. Compounds of the formula (XIV) may be prepared by the reduction of a compound of the formula (XV). The reduction may be carried out with any suitable hydride reducing agent or by hydrogenation. In a typical procedure, a solution of the compound of the formula (XV) in a suitable solvent, such as ethanol, is saturated with ammonia gas, treated with an appropriate hydrogenation catalyst such as 5% w/w palladium on charcoal and pressurised with hydrogen, preferably to 1034 kPa (150 psi). Compounds of the formula (XV) may be prepared by the reaction of a compound of the formula (XVI) with an appropriate primary amine. Typically, a solution of the compound (XVI) in a suitable solvent such as acetonitrile is treated with the amine at room temperature. An additional acid acceptor such as diphenylethylamine may optionally be added. Compounds of the formula (XVI) may be prepared by the substitution of the iodo group in a compound of the formula (XVII) with cyanide. Typically, a solution of the compound of the formula (XVII) in a suitable solvent (e.g. N,N-dimethylformamide) is treated with copper(II)cyanide and heated, preferably at a temperature in excess of 100° C. Compounds of the formula (XVII) are known in the art (e.g. see *J. Med. Chem.*, 1992, 35, 248 where $P^1$, $P^2$ and $P^3$ are each acetyl).

Alternatively, the compounds of the formula (I) may be prepared according to Scheme 3, wherein X is a leaving group, preferably chloro, by sulphonylation of a compound of formula (XVIII) with a compound of the formula (VII).

Scheme 3

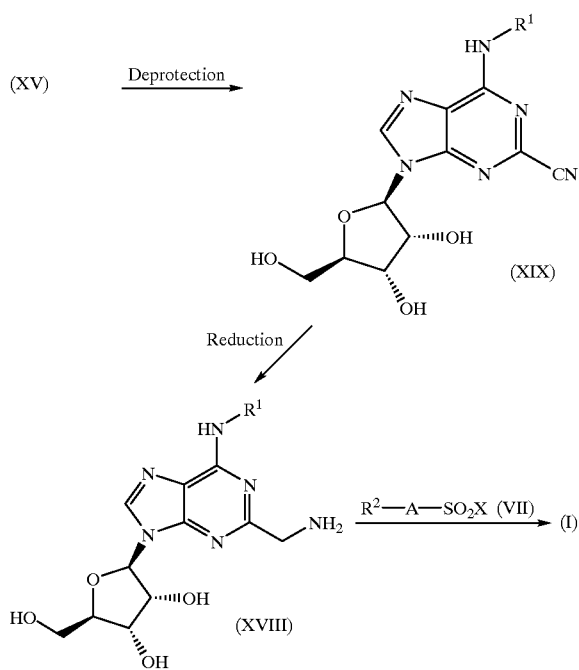

In a typical procedure, the compound of formula (XVIII) is dissolved in a suitable solvent such as 1,4-dioxan or tetrahydrofuran (with heating if necessary) and treated, typically at room temperature and under an atmosphere of nitrogen, with a sulphonylating agent of the formula (VII), optionally in the presence of an acid acceptor (e.g. triethylamine). Compounds of the formula (XVIII) may be prepared by the reduction of a compound of the formula (XIX). The reduction may be carried out with any suitable hydride reducing agent or by hydrogenation. In a typical procedure, a solution of the compound of formula (XIX) in a suitable solvent such as ethanol is saturated with ammonia gas, treated with an appropriate hydrogenation catalyst such as 5% w/w palladium on charcoal and pressurised with hydrogen, preferably to 1034 kPa (150 psi). Compounds of the formula (XIX) may be prepared by the deprotection of a compound of the formula (XV) according to methods known in the art [see for instance 'Protecting Groups in Organic Synthesis (Second Edition)', Theodora W. Green and Peter G. M. Wuts, John Wiley and Sons, 1991]. The protecting groups may be removed together, individually or in any combination thereof. In a typical example, where $P^1$, $P^2$ and $P^3$ are each acetyl, a solution of the compound of the formula (XV) in a suitable solvent such as ethanol is treated with a base such as ammonia at room temperature. In certain cases, deprotection and reduction of a compound of the formula (XV) to furnish a compound of the formula (XVIII) may be conveniently carried out together under reducing conditions. In a typical example, the compound of the formula (XV) is dissolved in a suitable solvent such as ethanol and the solution is saturated with ammonia prior to treatment with an appropriate hydrogenation catalyst such as palladium on carbon and pressurisation with hydrogen to 1034 kPa (150 psi).

Compounds of the formula (I) in which A is —$CH_2CH_2$— and $R^2$ is $NR^7R^8$ may also be prepared by the route shown in Scheme 4.

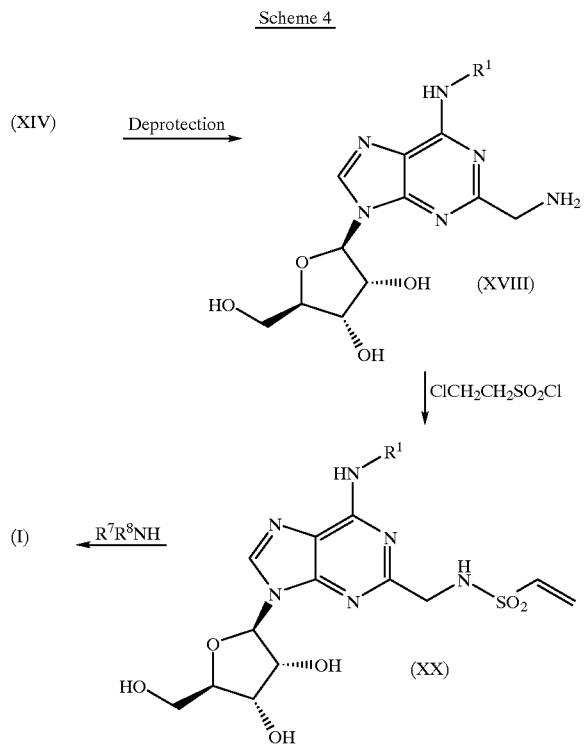

In Scheme 4, compounds of the formula (I) in which A is —$CH_2CH_2$— and $R^2$ is —$NR^7R^8$ may be prepared by the reaction of a compound of the formula (XX) with a compound of the formula $$R^7R^8NH \qquad (XXII).$$

In a typical procedure, the compound of the formula (XX) and the compound of the formula (XXII) are mixed, optionally in the presence of a suitable solvent. Preferably, the reaction mixture is heated, most preferably at the reflux temperature of the compound of the formula (XXII). Compounds of the formula (XXII) are either commercially available or easily prepared using standard procedures well known to those skilled in the art (e.g. the reductive condensation of an amine with a ketone or an aldehyde). Compounds of the formula (XX) may be prepared by the condensation of a compound of the formula (XVIII) with 2-chloroethanesulphonyl chloride. In a typical procedure, a solution of the compound of the formula (XVIII) and a base, preferably a tertiary amine base such as triethylamine, in a suitable solvent, such as dichloromethane, is treated with 2-chloroethanesulphonyl chloride. Compounds of the formula (XVIII) may be prepared by the deprotection of a compound of the formula (XIV) in which protecting groups $P^1$, $P^2$ and $P^3$ are as defined above. The protecting groups may be removed together, or singly in any combination thereof. Suitable conditions for the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$, $P^2$ and $P^3$ are each acetyl, the protecting groups may be removed by treating a solution of the compound of formula (XIV) in a suitable solvent, such as a mixture of water and methanol, with a base such as sodium carbonate, typically at room temperature.

Compounds of the formula (I) may also be interconverted using conventional functional group interconversion techniques.

All of the reactions and the preparations of novel starting materials used in the preceding methods are conventional and appropriate reagents and reaction conditions as well as procedures for isolating the desired products will be well-known to persons skilled in the art with reference to literature precedents and the Examples and Preparations sections below.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production is measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.01 to 100 mg/kg, preferably from 0.1 to 100 mg/kg (in single or divided doses).

Thus tablets or capsules of the compound of the formula (I) may contain from 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 to 4000 μg of a compound of the formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered, for example, by the use of a skin patch.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gammacyclodextrins are most commonly used and suitable examples are described in WO-A-91/11172, WO-A-94/02518 and WO-A-98/55148.

It is to be appreciated that all references herein to treatment include curative, palliative and prophylactic treatment.

Thus the invention provides:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition including a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament to treat a disease for which a A2a receptor agonist is indicated;

(vi) the use of a compound of the formula (I) or of a pharmaceutically acceptable salt, solvate or composition thereof, for the manufacture of an anti-inflammatory agent;

(vii) the use of a compound of the formula (I) or of a pharmaceutically acceptable salt, solvate or composition thereof, for the manufacture of a medicament for the treatment of a respiratory disease;

(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) the use of a compound of the formula (I) or of a pharmaceutically acceptable salt, solvate or composition thereof, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastrointestinal tract or a psychotic disorder, or for wound healing;

(x) a method of treatment of a mammal, including a human being, to treat a disease for which a A2a receptor agonist is indicated including treating said mammal with an effective amount of a compound of the formula (I) or with a pharmaceutically acceptable salt, solvate or composition thereof;

(xi) a method of treatment of a mammal, including a human being, to treat an inflammatory disease including treating said mammal with an effective amount of a compound of the formula (I) or with a pharmaceutically acceptable salt, solvate or composition thereof;

(xii) a method of treatment of a mammal, including a human being, to treat a respiratory disease including treating said mammal with an effective amount of a compound of the formula (I) or with a pharmaceutically acceptable salt, solvate or composition thereof;

(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) a method of treatment of a mammal, including a human being, to treat septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastrointestinal tract or a psychotic disorder, or for wound healing, including treating said mammal with an effective amount of a compound of the formula (I) or with a pharmaceutically acceptable salt, solvate or composition thereof; and (xv) certain novel intermediates disclosed herein.

The following Examples illustrate the preparation of the compounds of the formula (I):

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded in the thermospray ionisation mode. The following abbreviations have been used for common solvents: CDCl$_3$, deuterochloroform; DMSO, dimethylsulphoxide. The abbreviation psi means pounds per square inch. Where thin layer chromatography (TLC) has been used it refers to silica gel TLC using silica gel 60 F$_{254}$ plates, R$_f$ is the distance travelled by a compound divided by the distance travelled by the solvent front on a TLC plate. The abbreviation Ac has been used in place of acetyl and TBDMS means tert-butyldimethylsilyl.

EXAMPLE 1

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)-2-methyl-1-propanesulfonamide

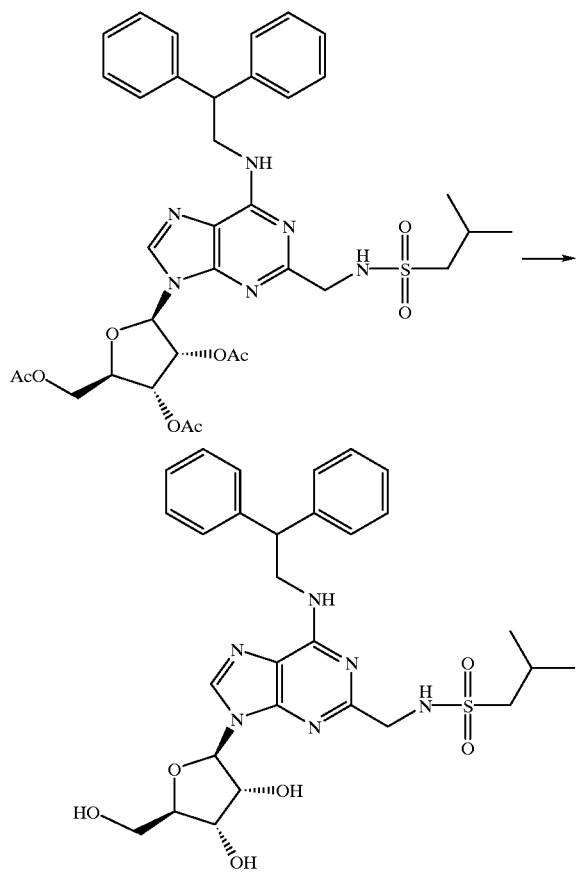

A solution of (2R,3R,4R,5R)-4-(acetyloxy)-2-[(acetyloxy) methyl]-5-(6-[(2,2-diphenylethyl)amino]-2-{[(isobutylsulfonyl)amino]methyl}-9H-purin-9-yl) tetrahydro-3-furanyl acetate (188 mg, 0.26 mmol)

(Preparation 9) and sodium carbonate (140 mg, 1.32 mmol) in a mixture of water (2 ml) and methanol (10 ml) was stirred at room temperature for 6 hours. The solvent was removed under reduced pressure and the residue partitioned between ethyl acetate and brine. The organic phase was separated and the solvent removed under reduced pressure. The residue was then purified by column chromatography on silica gel eluting with a gradient system of dichloromethane:methanol:0.88 ammonia (95:5:0.5 by volume) gradually changing to dichloromethane:methanol:0.88 ammonia (90:10:1 by volume) to afford the title compound (77 mg).

MS: 597 (MH$^+$); 619 (MNa$^+$).

$^1$H-NMR (CDCl$_3$) δ: 7.60 (1H, br s), 7.20–7.38 (10H, m), 6.02 (1H, br s), 5.91 (1H, br d), 5.81 (1H, t), 5.70 (1H, d), 4.83 (1H, br s), 4.50 (1H, d), 4.07–4.40 (7H, m), 3.90 (1H, d), 3.75 (1H, t), 3.32 (1H, s), 2.95 (2H, d), 2.26 (1H, m), 4.06 (6H, d).

Analysis: Found C, 57.54; H, 6.10; N, 13.76%; C$_{29}$H$_{36}$N$_6$O$_6$S. 0.5H$_2$O requires C, 57.52; H, 6.11; N, 13.88%.

EXAMPLE 2

N-{[9-[(2R,3R,4S,5R)-3,4-Dihydroxy-5-(hydroxymethyl)tetrahydro-2-furanyl]-6-(phenethylamino)-9H-purin-2-yl]methyl}benzenesulfonamide

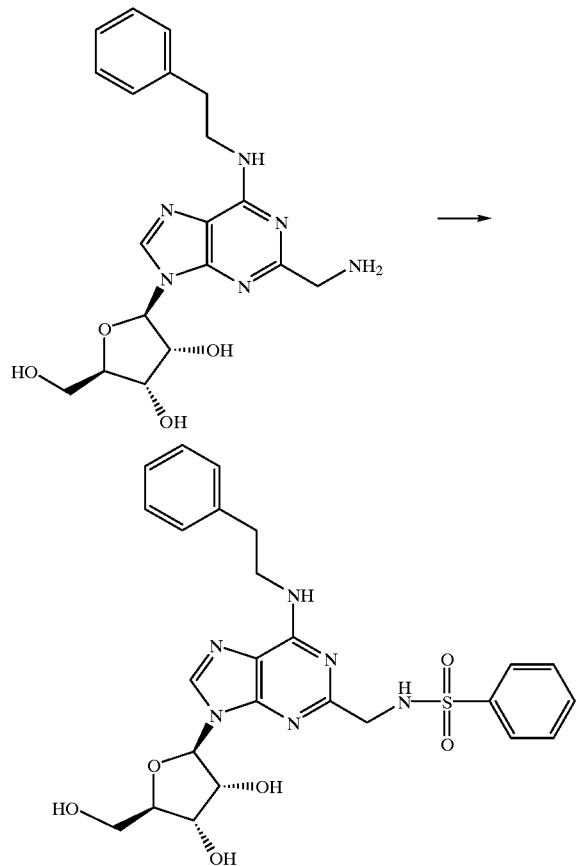

A solution of benzenesulfonyl chloride (0.067 g, 0.3 mmol) in dry tetrahydrofuran (2 ml) was added over 10 minutes to a stirred solution of (2R,3R,4S,5R)-2-[2-(aminomethyl)-6-(phenethylamino)-9H-purin-9-yl]-5-(hydroxymethyl)tetrahydro-3,4-furandiol (0.19 g, 0.48 mmol) (Preparation 12) and triethylamine (0.14 g, 1.39 mmol) in dry tetrahydrofuran (10 ml) at 0° C. under an atmosphere of nitrogen. The mixture was stirred at 0° C. for 15 minutes. The solvent was then removed under reduced pressure and the residue azeotroped with dichloromethane (×3). The residue was purified by column chromatography on silica gel eluting with dichloromethane:methanol:0.88 ammonia (92:8:0.4 by volume), to give the product which was triturated with diethyl ether, filtered and dried to afford the title compound as a solid (200 mg).

MS: 540 (MH$^+$).

$^1$H-NMR (CDCl$_3$) δ: 7.82 (2H, d), 7.63 (1H, s), 7.16–7.45 (8H, m), 6.02–6.22 (2H, m), 5.96 (1H, br s), 5.70 (1H, d), 4.82 (1H, m), 4.47 (1H, d), 4.02–4.34 (4H, m), 3.62–3.98 (4H, m), 3.37 (1H, s), 2.92 (2H, t).

EXAMPLE 3

N-({9-[(2R,3R,4S,5 R)-3,4-Dihydroxy-5-(hydroxymethyl)tetrahydro-2-furanyl]-6-[(1-naphthylmethyl)amino]-9H-purin-2-yl}methyl)benzenesulfonamide

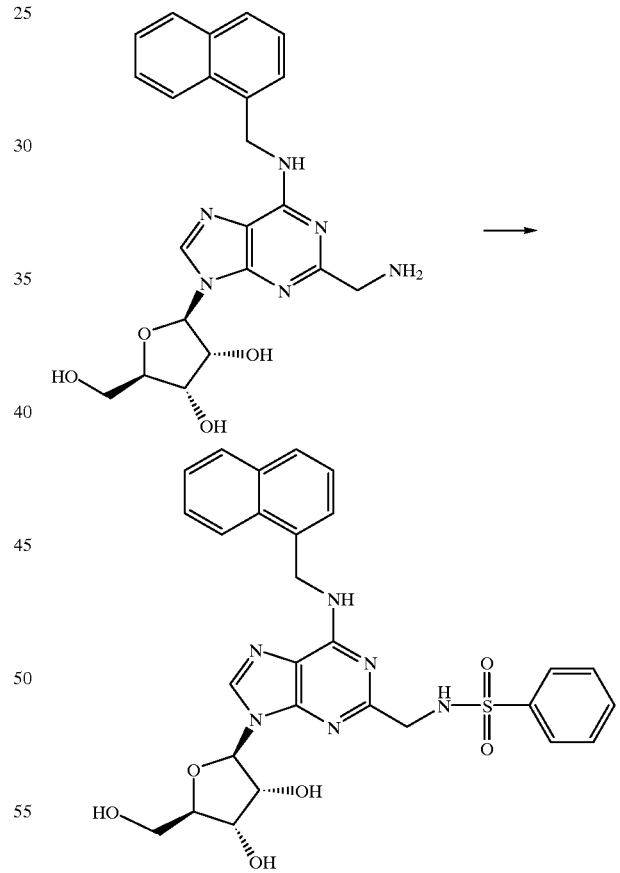

A suspension of (2R,3R,4S,5R)-2-{2-(aminomethyl)-6-[(1-naphthylmethyl)amino]-9H-purin-9-yl}-5-(hydroxymethyl)tetrahydro-3,4-furandiol (0.16 g, 0.37 mmol) (Preparation 15) in dioxan (28 ml) was heated gently until a solution was achieved. The solution was cooled to room temperature and treated with triethylamine (0.12 g, 1.19 mmol) followed by addition of a solution of benzenesulphonyl chloride (0.060 g, 0.34 mmol) in dioxan (2 ml)

over 10 minutes. The mixture was then stirred at room temperature for 30 minutes. The solvent was removed under reduced pressure and the residue azeotroped with dichloromethane. The residue was purified by column chromatography on silica gel eluting with dichloromethane:methanol:0.88 ammonia (92:8:0.4 by volume) to afford the title compound as a white solid (150 mg).

MS: 577 (MH+).

$^1$H-NMR (DMSO-$d_6$) δ:8.15–8.40 (3H, m), 7.20–7.98 (12H, m), 5.85 (1H, d), 5.38 (1H, d), 5.00–5.36 (4H, m), 4.52 (1H, q), 4.13 (1H, m), 4.00 (2H, s), 3.92 (1H, d), 3.42–3.72 (2H, m).

EXAMPLE 4

2-[Cyclopentyl(isopropyl)amino]-N-({9-[(2R,3R,4S,5R)-3,4-dihydroxy-5-(hydroxymethyl)tetrahydro-2-furanyl]-6-[(2,2-diphenylethyl)amino]-9H-purin-2-yl}methyl)ethanesulfonamide

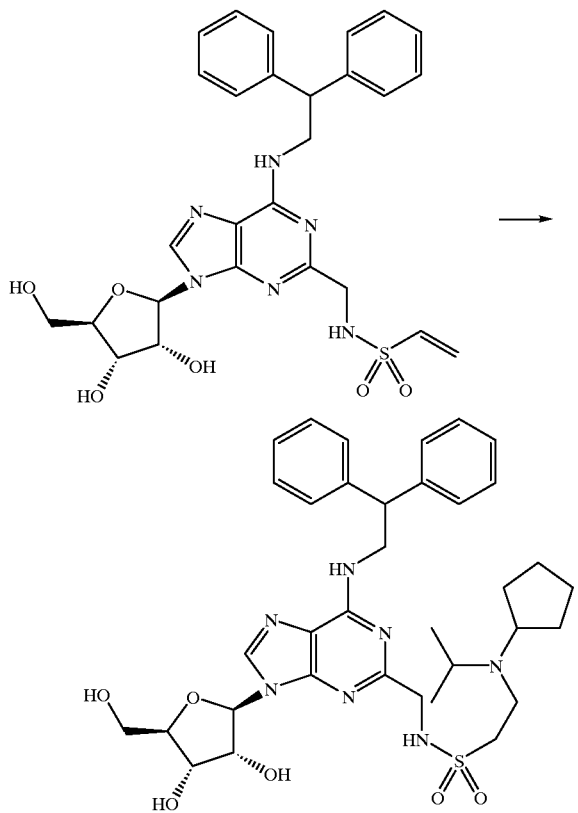

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)ethylenesulfonamide (60 mg, 0.11 mmol) (Preparation 16) was dissolved in N-isopropylcyclopentanamine (2 ml) (Preparation 17) and the reaction mixture was heated under reflux for two hours. The excess reagent was removed under reduced pressure and the residue was partitioned between dichloromethane (50 ml) and water (30 ml). The organic layer was evaporated and dried (anhydrous magnesium sulphate) and the residue was purified by column chromatography on silica gel eluting with dichloromethane:methanol:ammonia (92:7:1 by volume) to give the title compound (13 mg) as an oil.

MS: 695 (MH+).

$^1$H-NMR (CD$_3$OD) δ: (1H, s), 7.35–7.20 (10H, m), 6.00–5.95 (1H, m), 4.70–4.65 (1H, m), 4.55–4.50 (1H, m), 4.35–4.25 (6H, m), 4.15 (1H, s), 3.90–3.85 (1H, m), 3.75–3.70 (1H, m), 3.15–3.10 (2H, m), 3.00–2.90 (2H, m), 2.90–2.80 (2H, m), 1.70–1.60 (2H, m), 1.60–1.50 (2H, m), 1.50–1.40 (2H, m), 1.35–1.15 (2H, m), 0.9–0.85(6H, m).

The following Preparations describe the preparation of certain intermediates used in the preceding Examples.

PREPARATION 1

2,6-Dichloro-9-tetrahydro-2H-pyran-2-yl-9H-purine

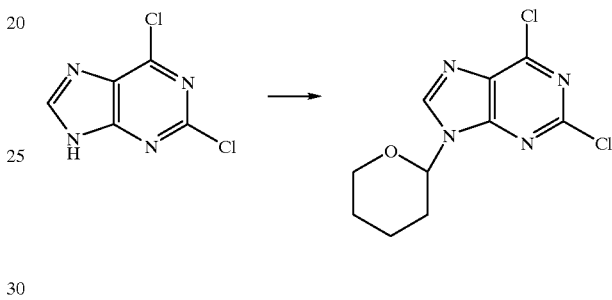

2,6-Dichloro-9H-purine (20 g, 0.11 mol) and 4-toluenesulphonic acid monohydrate (0.2 g) were dissolved in ethyl acetate (300 ml), the mixture was heated to 50° C. and a solution of 2,3-dihydropyran (12.6 ml, 0.14 mol) in ethyl acetate (50 ml) was added slowly over 30 min. The reaction mixture was then cooled to room temperature, water (100 ml) was added and the pH of the solution was adjusted to 7 with a saturated aqueous solution of sodium hydrogen carbonate. The layers were separated and the organic layer was washed sequentially with water and brine, dried over anhydrous magnesium sulphate, filtered and evaporated under reduced pressure. The residue was azeotroped from pentane (×2) to afford the title compound as a slightly impure white solid (30.9 g).

$^1$H-NMR (CDCl$_3$) δ: 8.30 (1H, s), 5.75 (1H, dd), 4.25–4.15 (1H, m), 3.85–3.70 (1H, m), 2.20–1.60 (6H, m).

PREPARATION 2

2-Chloro-N-(2,2-diphenylethyl)-9-tetrahydro-2H-pyran-2-yl-9H-purin-6-amine

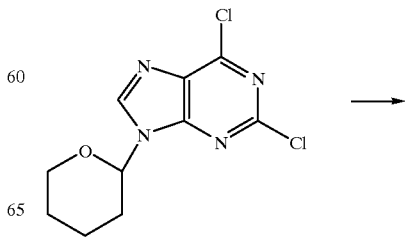

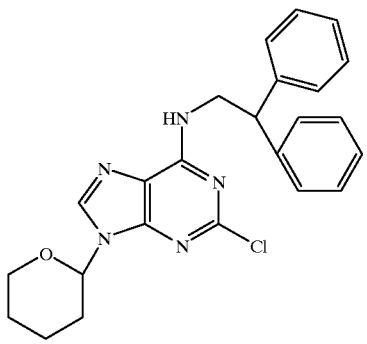

A solution of 2,6-dichloro-9-tetrahydro-2H-pyran-2-yl-9H-purine (Preparation 1) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture was heated at reflux for 3 hours. The solvent was removed under reduced pressure and the residue was azeotroped from ethyl acetate. The residue was purified by column chromatography on silica gel eluting with a gradient system of ethyl acetate:hexane (40:60 by volume) gradually changing to ethyl acetate:hexane (60:40 by volume) to afford the title compound as a foam (49.7 g).

$^1$H-NMR (CDCl$_3$) δ: 7.95–7.75 (1H, br s), 7.35–7.15 (10H, m), 5.80–5.70 (1H, br s), 5.65 (1H, d), 4.35 (1H, m), 4.30–4.18 (1H, br s), 4.10 (1H, d), 3.70 (1H, t), 2.05–1.95 (2H, m), 1.95–1.80 (1H, m), 1.80–1.55 (3H, m).

PREPARATION 3

N(2,2-Diphenylethyl)-2-(methylsulfanyl)-9-tetrahydro-2H-pyran-2-yl-9H-purin-6-amine

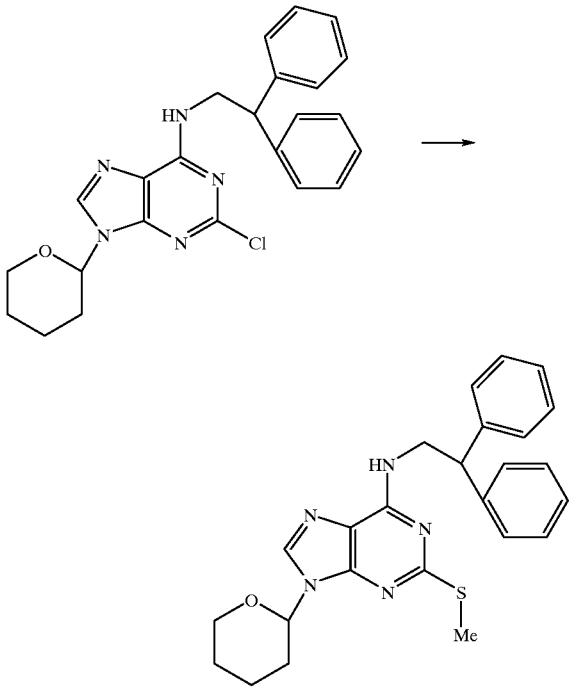

A solution of 2-chloro-N-(2,2-diphenylethyl)-9-tetrahydro-2H-pyran-2-yl-9H-purin-6-amine (Preparation 2) (49.7 g, 0.11 mol) in dry N,N-dimethylformamide (200 ml) was treated with sodium thiomethoxide (10 g, 0.14 mol) and the resulting mixture heated under an atmosphere of nitrogen at 100° C. for 90 minutes. The mixture was stirred at room temperature for 72 hours and then reheated to 100° C. for a further 2 hours. The reaction mixture was cooled and diluted with water (1000 ml). A suspension was formed which was extracted into diethyl ether (×2). The combined organic layers were washed sequentially with water and brine, dried over anhydrous magnesium sulphate, filtered and evaporated under reduced pressure. The residue was azeotroped from diethyl ether and then pentane to afford the title compound as a foam (48.9 g).

$^1$H-NMR (CDCl$_3$) δ: 7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

PREPARATION 4

N(2,2-Diphenylethyl)-2-(methylsulfonyl)-9-tetrahydro-2H-pyran-2-yl-9H-purin-6-amine

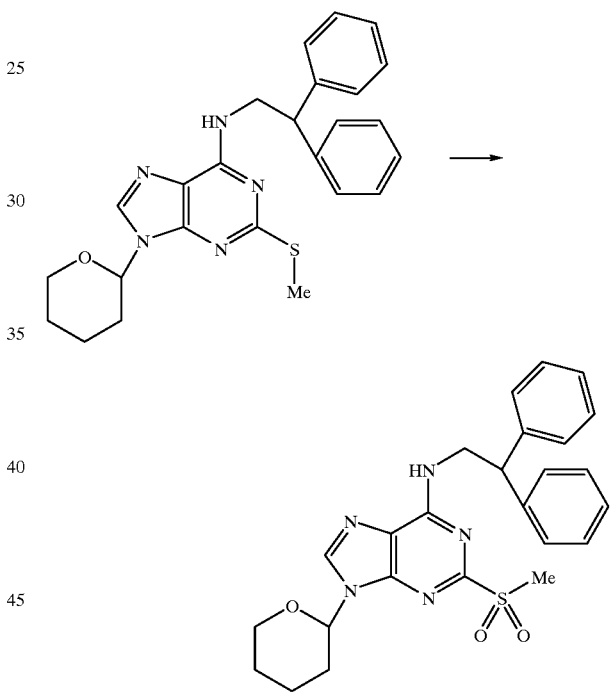

A solution of Oxone (trade mark) (potassium peroxymonosulphate) (44 g, 71.7 mmol) in water (200 ml) was added dropwise over 2 hours to a solution of N-(2,2-diphenylethyl)-2-(methylsulfanyl)-9-tetrahydro-2H-pyran-2-yl-9H-purin-6-amine (Preparation 3) (25 g, 56.2 mmol) and sodium hydrogen carbonate (20 g, 238 mmol) in acetone (1000 ml) and water (250 ml). The resulting mixture was stirred at room temperature for 24 hours, filtered and the residue washed with acetone. The acetone was removed from the filtrate under reduced pressure and the resulting aqueous residue extracted with ethyl acetate and then dichloromethane. The combined organic layers were washed with brine, dried with anhydrous magnesium sulphate, filtered and evaporated under reduced pressure. The residue was triturated with diethyl ether, filtered, washed with diethyl ether and pentane and then dried to afford the title compound as a white solid (20.32 g).

¹H-NMR (CDCl₃) δ : 8.00 (1H, s), 7.35–7.15 (1 OH, m), 6.05–5.95 (1H, br s), 5.75 (1H, d), 4.40–4.35 (1H, m), 4.35–4.20 (2H, br s), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

PREPARATION 5

6-[(2,2-Diphenylethyl)amino]-9-tetrahydro-2H-pyran-2-yl-9H-purine-2-carbonitrile

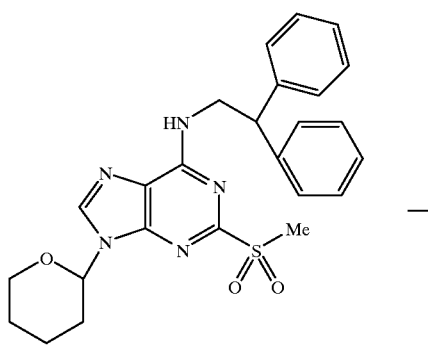

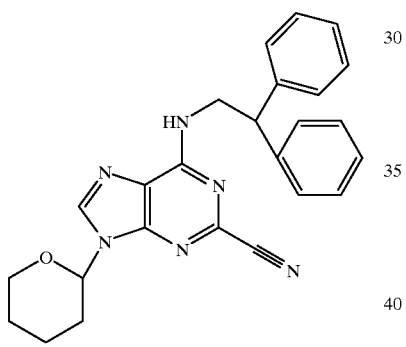

A solution of N-(2,2-diphenylethyl)-2-(methylsulfonyl)-9-tetrahydro-2H-pyran-2-yl-9H-purin-6-amine (Preparation 4) (20.1 g, 42.1 mmol) in dry N,N-dimethylformamide (100 ml) was treated with potassium cyanide (5.5 g, 84.6 mmol) and the mixture was heated at 120° C. for 24 hours under a nitrogen atmosphere. The mixture was then cooled to room temperature, poured into water (1000 ml) and stirred for a further 1 hour. The resultant solid was slowly filtered and washed several times with water. The solid was then dissolved in dichloromethane and the resulting solution was washed with water, dried with anhydrous magnesium sulphate, filtered and evaporated under reduced pressure. The residue was azeotroped from diethyl ether twice to afford the title compound as an oil (17 g).

¹H-NMR (CDCl₃) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90(3H, m), 1.90–1.60 (3H, m).

PREPARATION 6

N-[2-(Aminomethyl)-9-tetrahydro-2H-pyran-2-yl-9H-purin-6-yl]-N-(2,2-diphenylethyl)amine

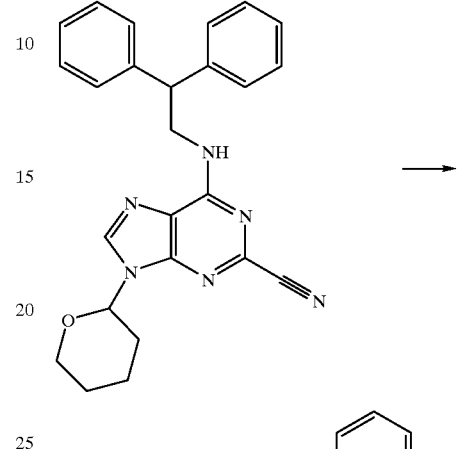

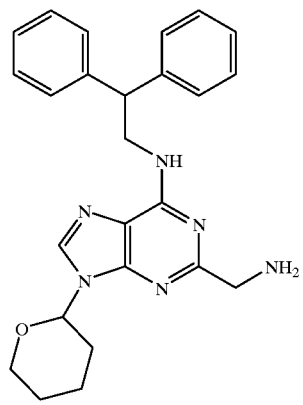

A solution of 6-[(2,2-diphenylethyl)amino]-9-tetrahydro-2H-pyran-2-yl-9H-purine-2-carbonitrile (5.70 g, 13.18 mmol) (Preparation 5) in ethanol (200 ml) saturated with ammonia gas was treated with Pearlmann's catalyst (1.00 g), pressurised to 60 psi with hydrogen in a sealed vessel and stirred at room temperature for 30 hours. The mixture was filtered through a pad of Arbocel (trade mark) and the solvent was removed under reduced pressure. The residue was azeotroped from dichloromethane (×2) and then purified by column chromatography on silica gel eluting with dichloromethane:methanol (95:5 by volume) gradually changing to dichloromethane:methanol:0.88 ammonia (90:10:0.5 by volume) to afford the title compound (4.34 g).

MS: 429 (MH⁺).

¹H-NMR (CDCl₃) δ: 7.84 (1H, s), 7.14–7.36 (10H, m), 5.70 (1H, d), 5.50–5.70(1H, br s), 4.20–4.42 (3H, m), 4.14 (1H, d), 3.95 (2H, s), 3.78 (1H, t), 1.90–2.20 (5H, m), 1.50–1.88 (3H, m).

PREPARATION 7

N-({6-[(2,2-Diphenylethyl)amino]-9-tetrahydro-2H-pyran-2-yl-9H-purin-2-yl}methyl)-2-methyl-1-propanesulfonamide

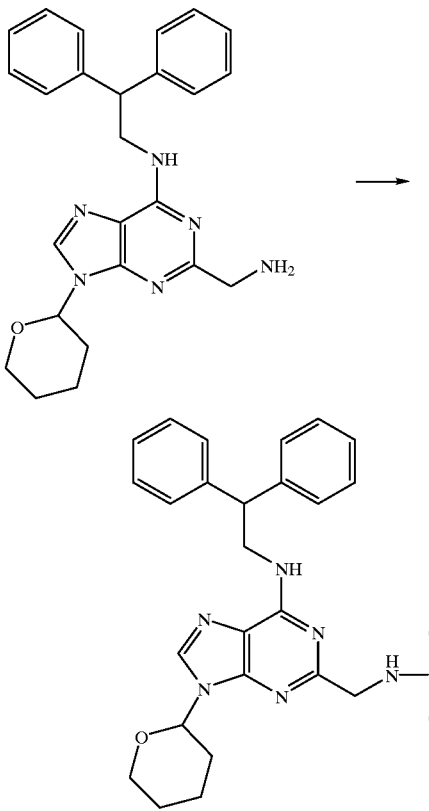

A solution of N-[2-(aminomethyl)-9-tetrahydro-2H-pyran-2-yl-9H-purin-6-yl]-N-(2,2-diphenylethyl)amine (3.70 g, 8.63 mmol) (Preparation 6) and triethylamine (2.20 g, 21.78 mmol) in dry dichloromethane (20 ml) was treated with 2-methyl-1-propanesulfonyl chloride (1.48 g, 9.46 mmol) and the mixture was stirred at room temperature for 18 hours. TLC indicated that some starting material still remained and so further 2-methyl-1-propanesulfonyl chloride (0.2 g, 1.28 mmol) was added and the mixture was stirred at room temperature for 1 hour. The solvent was removed under reduced pressure and the residue was purified by column chromatography on silica gel eluting with dichloromethane:methanol (98:2 by volume) to afford the title compound as a foam (4.4 g).

MS: 549 (MH+).

$^1$H-NMR (CDCl$_3$) δ: 7.86 (1H, s), 7.16–7.36 (10H, m), 5.74 (1H, br s), 5.64 (1H, d), 5.57 (1H, t), 4.18–4.46 (5H, m), 4.14 (1H, d), 3.77 (1H, t), 2.92 (2H, d), 2.28 (1H, m), 1.92–2.10 (3H, m), 1.58–1.88 (3H, m), 1.03 (6H, d).

PREPARATION 8

N-({6-[(2,2-Diphenylethyl)amino]-9H-purin-2-yl}methyl)-2-methyl-1-propanesulfonamide hydrochloride

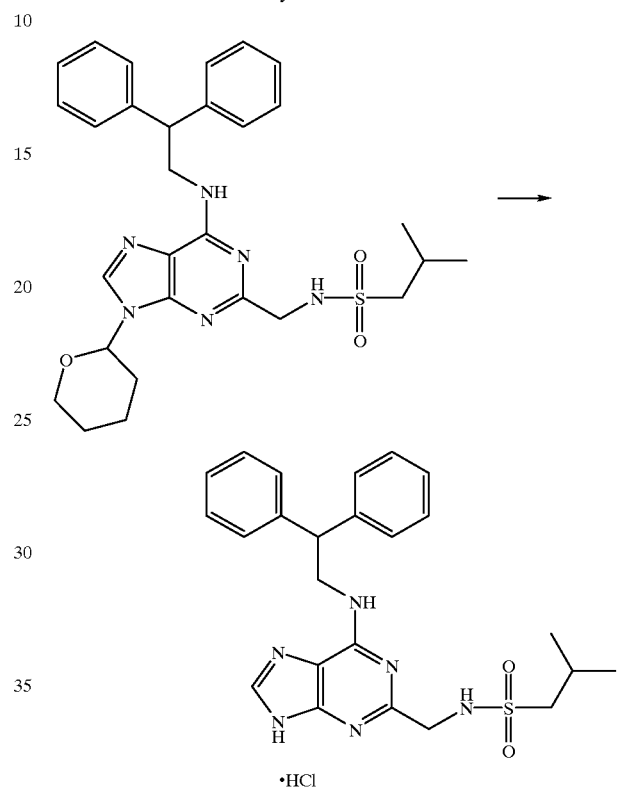

A solution of N-({6-[(2,2-diphenylethyl)amino]-9-tetrahydro-2H-pyran-2-yl-9H-purin-2-yl}methyl)-2-methyl-1-propanesulfonamide (4.30 g, 7.84 mmol) (Preparation 7) in ethanol (100 ml) was heated to 37° C. and then treated with hydrochloric acid (2N, 15 ml). The mixture was left to stand at room temperature for 18 hours, after which time a crystalline precipitate was filtered off, washed with ethanol (10 ml) and dried to afford the title compound as a solid (3.0 g).

$^1$H-NMR (DMSO-d$_6$) δ: 8.48 (1H, br s), 7.75 (1H, br s), 7.37 (4H, d), 7.27 (4H, dd), 7.16 (2H, dd), 4.56 (1H, t), 4.20–4.40 (4H, m), 2.95 (2H, d), 2.10 (1H, m), 0.95 (6H, d).

PREPARATION 9

(2R,3R,4R,5R)-4-(Acetyloxy)-2-[(acetyloxy)methyl]-5-(6-[(2,2-diphenylethyl)amino]-2-{[(isobutylsulfonyl)amino]methyl}-9H-purin-9-yl)tetrahydro-3-furanyl acetate

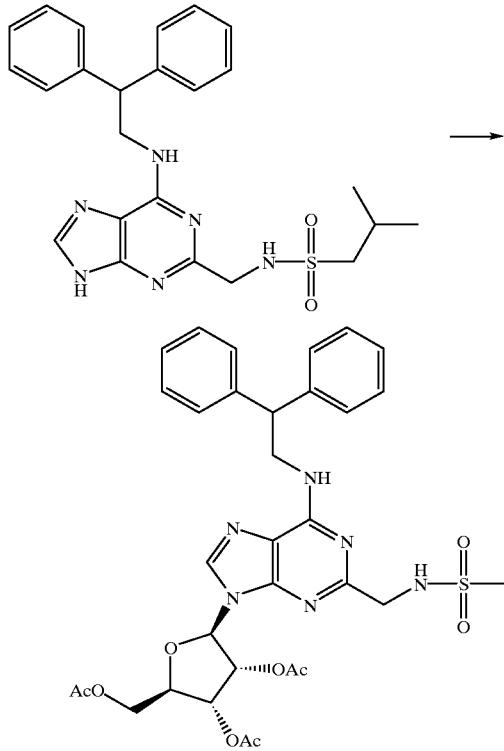

A suspension of N-({6-[(2,2-diphenylethyl)amino]-9H-purin-2-yl}methyl)-2-methyl-1-propanesulfonamide hydrochloride (Preparation 8) (0.21 g, 0.42 mmol) in 1,1,1-trichloroethane (10 ml) was treated with N,O-bis(trimethylacetamide) (0.6 ml, 2.45 mmol) and the mixture was heated under reflux for 2 hours. The solvent was removed under reduced pressure and the residue was azeotroped with toluene (×2). The residue was dissolved in toluene (10 ml) and treated with the β-D-ribofuranose-1,2,3,5-tetraacetate (0.16 g, 0.50 mmol) and trimethylsilyltriflate (0.1 ml, 0.5 mmol). The mixture was then heated at reflux for 4 hours. The mixture was diluted with ethyl acetate, washed sequentially with saturated aqueous sodium hydrogen carbonate solution and brine and evaporated under reduced pressure. The residue was purified by column chromatography on silica gel eluting with a gradient system of dichloromethane:methanol (98:2 by volume) gradually changing to dichloromethane:methanol (95:5 by volume) to afford the title compound as a 1:3 mixture of α-and β-anomers (188 mg).

MS: 723 (MH$^+$); 745 (MNa$^+$).

$^1$H-NMR (CDCl$_3$) δ: 7.97 (0.25H, br s), 7.76 (0.75H, br s), 7.15–7.37 (10H, m), 7.25 (2.25H, m), 5.88 (1.75H, m), 5.73 (0.75H, m), 5.51 (0.25H, m), 4.34–4.63 (8H, m), 2.95 (2H, m), 2.28 (3H, s), 2.06–2.20 (4H, m), 2.00 (3H, s), 1.05 (6H, d).

PREPARATION 10

(2R,3R,4R,5R)-4-(Acetyloxy)-2-[(acetyloxy)methyl]-5-(6-chloro-2-cyano-9H-purin-9-yl)tetrahydro-3-furanyl acetate

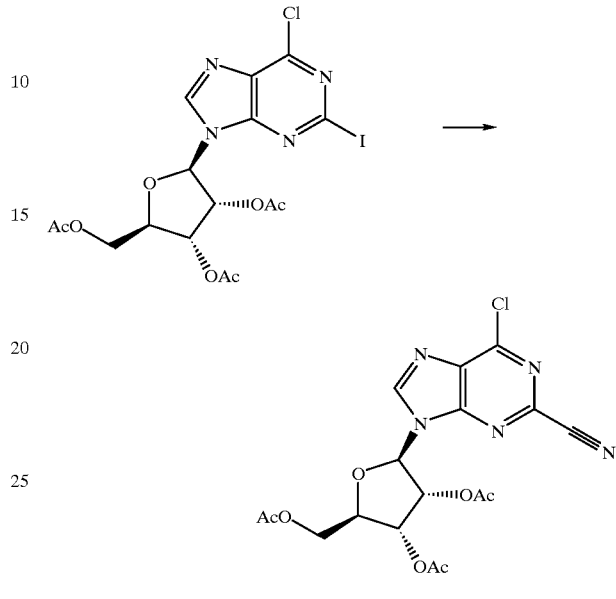

A mixture of (2R,3R,4R,5R)-4-(acetyloxy)-2-[(acetyloxy)methyl]-5-(6-chloro-2-iodo-9H-purin-9-yl)tetrahydro-3-furanyl acetate (*J. Med. Chem.*, 1992, 35, 248) (0.5 g, 0.93 mmol) and copper (II) cyanide (0.11 g, 1.23 mmol) in N,N-dimethylformamide was heated at 115° C. for 90 minutes. The solvent was removed under reduced pressure and the residue was purified by column chromatography on silica gel eluting with dichloromethane:ethyl acetate (4:1 by volume) to give a product which was then azeotroped sequentially with dichloromethane and diethyl ether to afford the title compound as a solid (0.22 g).

MS: 438 (MH$^+$).

$^1$H-NMR (CDCl$_3$) δ: 8.50 (1H, s), 6.28 (1H, d), 5.78 (1H, t), 5.53 (1H, m), 4.52 (1H, m), 4.42 (2H, m), 2.20 (3H, s), 2.17 (3H, s), 2.10 (3H, s).

PREPARATION 11

(2R,3R,4R,5R)-4-(Acetyloxy)-2-[(acetyloxy)methyl]-5-[2-cyano-6-(phenethylamino)-9H-purin-9-yl]tetrahydro-3-furanyl acetate

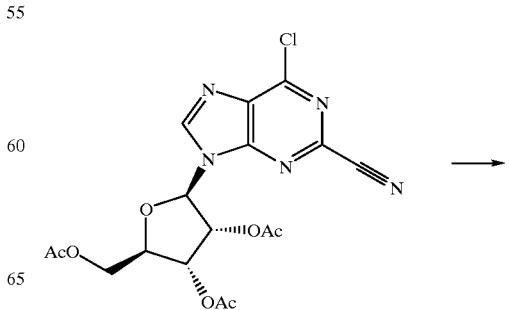

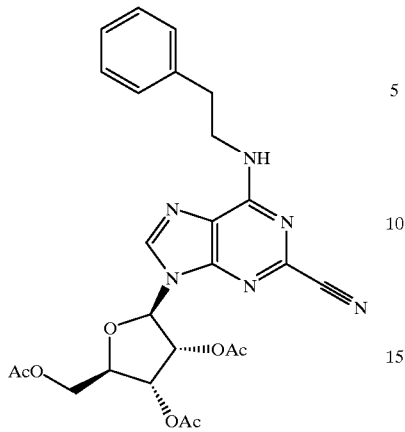

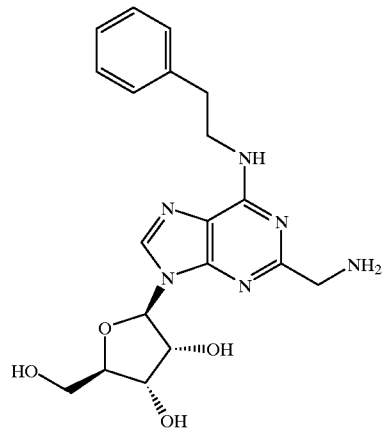

A solution of (2R,3R,4R,5R)-4-(acetyloxy)-2-[(acetyloxy)methyl]-5-(6-chloro-2-cyano-9H-purin-9-yl)tetrahydro-3-furanyl acetate (1.96 g, 4.48 mmol) (Preparation 10) and triethylamine (1.8 g, 17.8 mmol) in acetonitrile (20 ml) was treated with phenethylamine (0.60 g, 4.96 mmol) and the mixture was stirred at room temperature under a nitrogen atmosphere for 2 hours. The solvent was removed under reduced pressure and the residue was partitioned between dichloromethane (75 ml) and water (20 ml). The organic phase was separated and the solvent was removed under reduced pressure. The foam was purified by column chromatography on silica gel eluting with dichloromethane:ethyl acetate (4:1 by volume) to give a product which was then azeotroped with diethyl ether to afford the title compound as a foam (2.05 g).

MS: 523 (MH$^+$).

$^1$H-NMR (CDCl$_3$) δ: 8.00 (1H, s), 7.17–7.35 (5H, m), 6.16 (1H, d), 6.03 (1H, br s), 5.77 (1H, m), 5.57 (1H, m), 4.34–4.47 (3H, m), 3.80–4.00 (2H, br s), 2.98 (2H, m), 2.16 (3H, s), 2.14 (3H, s), 2.08 (3H, s).

PREPARATION 12

(2R,3R,4S,5R)-2-[2-(Aminomethyl)-6-(phenethylamino)-9H-purin-9-yl]-5-(hydroxymethyl)tetrahydro-3,4-furandiol

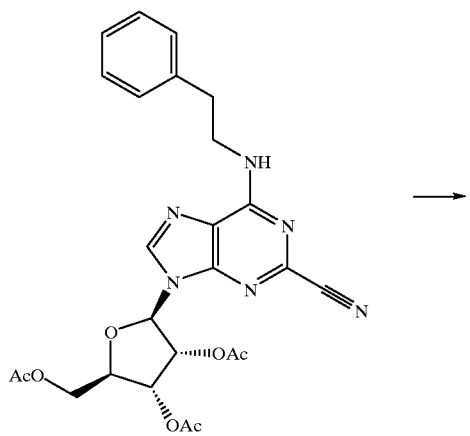

A solution of (2R,3R,4R,5R)-4-(acetyloxy)-2-[(acetyloxy)methyl]-5-[2-cyano-6-(phenethylamino)-9H-purin-9-yl]tetrahydro-3-furanyl acetate (1.0 g, 1.91 mmol) (Preparation 11) in ethanol (40 ml) saturated with ammonia gas was treated with 5% w/w palladium on charcoal (0.50 g), pressurised to 1034 kPa (150 psi) with hydrogen in a sealed vessel and stirred at room temperature for 18 hours. TLC analysis showed that some starting material still remained and therefore further 5% w/w palladium on charcoal (0.25 g) and ethanol (20 ml) saturated with ammonia were added and the mixture was again pressurised to 1034 kPa (150 psi) with hydrogen in a sealed vessel and stirred at room temperature for 18 hours. The mixture was filtered through a pad of Arbocel (trade mark) and the filtrate was evaporated under reduced pressure. The residue was azeotroped from dichloromethane, then purified by column chromatography on silica gel eluting with dichloromethane:methanol:0.88 ammonia (90:10:0.5 by volume) to afford the title compound as a white solid (340 mg).

MS: 401 (MH$^+$).

$^1$H-NMR (DMSO-d$_6$) δ: 8.28 (1H, br s), 7.91 (1H, br s), 7.14–7.33 (5H, m), 5.90 (1H, d), 5.38 (1H, br s), 5.17 (1H, br s), 4.61 (1H, br s), 4.13 (1H, br s), 3.95 (1H, s), 3.73 (5H, m), 3.66 (1H, dd), 3.52 (1H, dd), 2.90 (2H, t).

PREPARATION 13

(2R,3R,4R,5R)-4-(Acetyloxy)-2-[(acetyloxy)methyl]-5-{2-cyano-6-[(1-naphthylmethyl)amino]-9H-purin-9-yl}tetrahydro-3-furanyl acetate

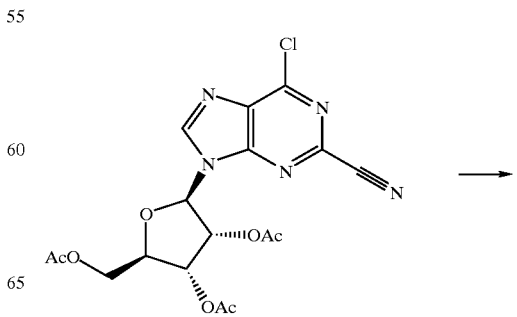

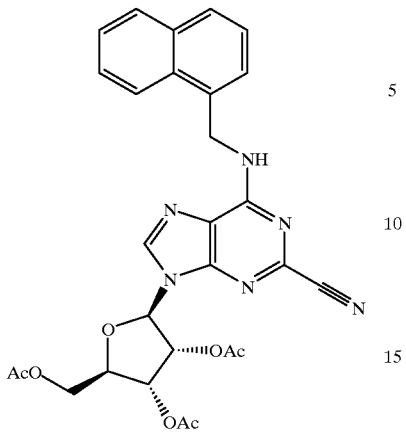

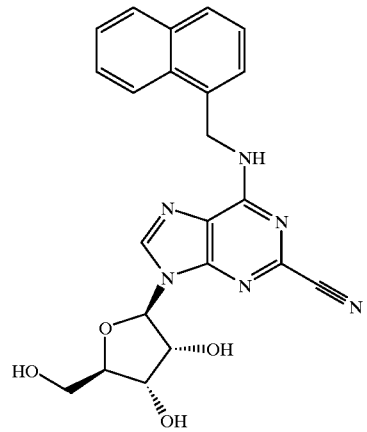

A solution of (2R,3R,4R,5R)-4-(acetyloxy)-2-[(acetyloxy)methyl]-5-(6-chloro-2-cyano-9H-purin-9-yl)tetrahydro-3-furanyl acetate (3.0 g, 6.86 mmol) (Preparation 10), 1-naphthalenemethylamine (1.2 g, 7.63 mmol), and triethylamine (2.8 g, 27.72 mmol) in acetonitrile (30 ml) was left to stand at room temperature for 2 hours during which time a fine precipitate slowly formed. The solvent was removed under reduced pressure and the residue partitioned between dichloromethane (150 ml) and water (50 ml). The organic phase was separated and the solvent was evaporated under reduced pressure The residue was purified by column chromatography on silica gel eluting with dichloromethane-:ethyl acetate (4:1 by volume) to give a product which was azeotroped with dichloromethane to afford the title compound as a foam (3.6 g).

MS: 559 (MH+).

$^1$H-NMR (CDCl$_3$) δ: 7.78–8.10 (4H, m), 7.38–7.62 (4H, m), 6.22 (1H, br s), 6.16 (1H, d), 5.78 (1H, t), 5.56 (1H, m), 5.24 (2H, br s), 4.36–4.48 (3H, m), 2.18 (3H, s), 2.15 (3H, s), 2.10 (3H, s).

A solution of (2R,3R,4R,5R)-4-(acetyloxy)-2-[(acetyloxy)methyl]-5-{2-cyano-6-[(1-naphthylmethyl)amino]-9H-purin-9-yl}tetrahydro-3-furanyl acetate (3.5 g, 6.27 mmol) (Preparation 13) in ethanol (120 ml) was saturated with ammonia gas and stirred at room temperature for 4 days. The solvent was removed under reduced pressure and the residue was triturated with water (100 mls), filtered and dried to afford the title compound as a solid (2.4 g).

MS: 433 (MH+).

$^1$H-NMR (DMSO-d$_6$) δ: 9.12 (1H, br s), 8.67 (1H, s), 8.24 (1H, d), 7.94 (1H, d), 7.82 (1H, m), 7.34–7.63 (4H, m), 5.91 (1H, d), 5.50 (1H, br s), 4.90–5.30 (4H, m), 4.53 (1H, m), 4.14 (1H, br s), 3.95 (1H, m), 3.60 (2H, m).

PREPARATION 14

9-[(2R,3R,4S,5R)-3,4-Dihydroxy-5-(hydroxymethyl)tetrahydro-2-furanyl]-6-[(1-naphthylmethyl)amino]-9H-purine-2-carbonitrile

PREPARATION 15

(2R,3R,4S,5R)-2-{2-(Aminomethyl)-6-[(1-naphthylmethyl)amino]-9H-purin-9-yl}-5-(hydroxymethyl)tetrahydro-3,4-furandiol

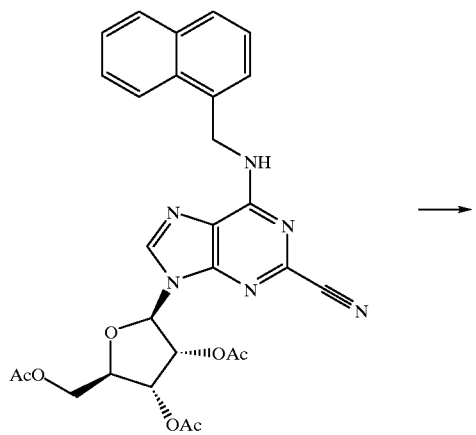

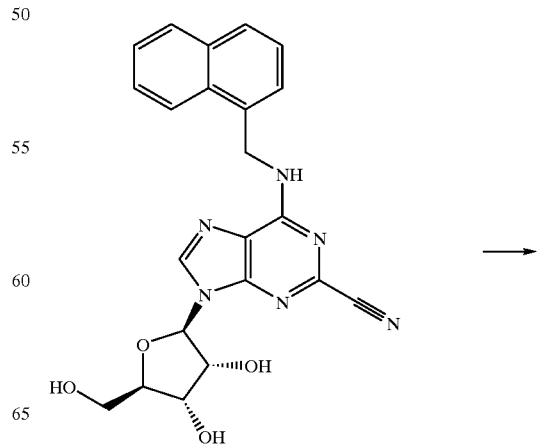

-continued

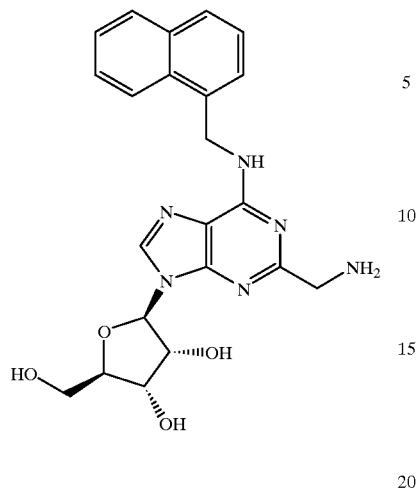

A solution of 9-[(2R,3R,4S,5R)-3,4-dihydroxy-5-(hydroxymethyl)tetrahydro-2-furanyl]-6-[(1-naphthylmethyl)amino]-9H-purine-2-carbonitrile (0.75 g, 1.74 mmol) (Preparation 14) in ethanol (30 ml) was saturated with ammonia gas, treated with 5% w/w palladium on charcoal (0.50 g), pressurised to 1034 kPa (150 psi) with hydrogen in a sealed vessel and stirred at room temperature for 42 hours. TLC analysis indicated that some starting material still remained and therefore further 5% w/w palladium on charcoal (0.30 g) and ethanol (10 ml) saturated with ammonia gas were added. The mixture was re-pressurised to 1034 kPa (150 psi) with hydrogen in a sealed vessel and stirred at room temperature for 24 hours. The mixture was filtered through a pad of Arbocel (trade mark) and the filtrate was evaporated under reduced pressure. The residue was purified by column chromatography on silica gel eluting with a gradient system of dichloromethane:methanol:0.88 ammonia (90:10:0.5 by volume) gradually changing to dichloromethane:methanol:0.88 ammonia (85:15:0.75 by volume) to afford the title compound (0.18 g).

MS: 437 (MH+).

$^1$H-NMR (DMSO-$d_6$) δ: 8.42 (1H, br s), 8.28 (2H, br s), 7.93 (1H, d), 7.80 (1H, d), 7.36–7.60 (4H, m), 5.88 (1 H, d), 5.38 (1H, br s), 5.18 (3H, br s), 4.60 (1H, br m), 4.13 (1H, br s), 3.95 (1H, m), 3.71 (2H, s), 3.63 (1H, dd), 3.57 (1H, dd).

PREPARATION 16

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)ethylenesulfonamide

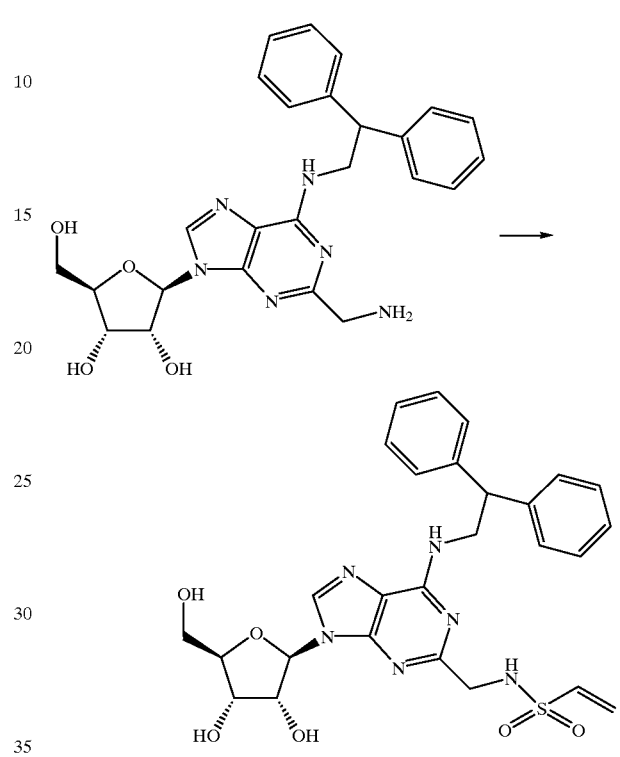

2-Chloroethanesulfonyl chloride (0.06 ml, 0.58 mmol) was added to a solution of (2R,3R,4S,5R)-2-{2-(aminomethyl)-6-[(2,2-diphenylethyl)amino]-9H-purin-9-yl}-5-(hydroxymethyl)tetrahydro-3,4-furandiol (250 mg, 0.52 mmol) (Preparation 19) and triethylamine (0.15 ml, 1.1 mmol) in dichloromethane (5 ml). The reaction mixture was stirred for two hours at room temperature then diluted with more dichloromethane (50 ml) and washed with water (50 ml). The organic layer was dried (anhydrous magnesium sulphate) and the solvent was evaporated to give a residue that was purified by column chromatography on silica gel eluting with methanol:dichloromethane (1:19 by volume) increasing in polarity to methanol:dichloromethane (1:9 by volume). The solvent was removed under reduced pressure to give the title compound (65 mg) as an oil.

$^1$H-NMR (CD$_3$OD) δ: 8.15 (1H, s), 7.40–7.15 (10H, m), 6.70–6.55 (1H, m), 6.15–6.05 (1H, m), 6.00–5.95 (1H, m), 5.80–5.75 (1H, m), 4.75–4.70 (1H, m), 4.55–4.50 (1H, m), 4.35–4.15 (6H, m), 3.95–3.85 (1H, m), 3.80–3.70 (1H, m).

PREPARATION 17

N-Isopropylcyclopentanamine

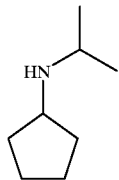

Sodium triacetoxyborohydride (33.76 g, 0.16 mol) was added to a solution of cyclopentylamine (15 ml, 0.15 mol) in acetone (500 ml). The reaction mixture was stirred at room temperature for 24 hr then the solvent was removed and the reaction mixture was partitioned between ethyl acetate (400 ml) and 2M aqueous sodium hydroxide (150 ml). The organic layer was separated, dried (anhydrous magnesium sulphate) and evaporated under reduced pressure to give the title compound (12 g) as a liquid.

$^1$H-NMR (CD$_3$OD) δ: 3.20–3.10 (1H, m), 2.95–2.80 (1H, m), 1.95–1.80 (2H, m), 1.75–1.45 (4H, m), 1.35–1.20 (2H, m), 1.10–1.00 (6H, m).

PREPARATION 18

(2R,3R,4R,5R)-4-(Acetyloxy)-2-[(acetyloxy)methyl]-5-{2-cyano-6-[(2,2-diphenylethyl)amino]-9H-purin-9-yl}tetrahydro-3-furanyl acetate

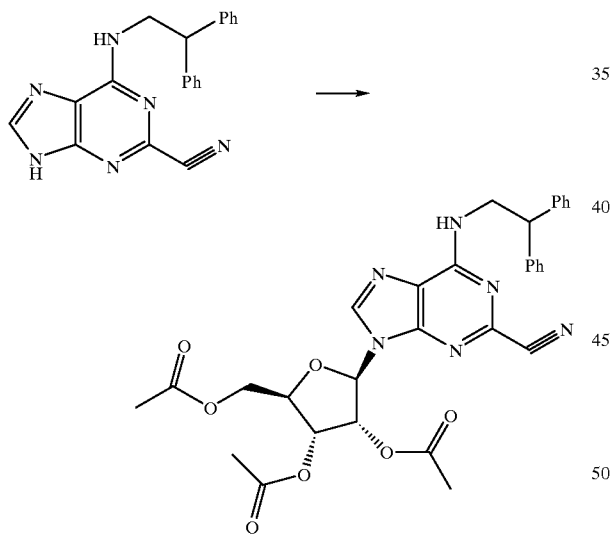

N,O-Bistrimethylsilylacetamide (44 ml, 0.18 mol) was added to a suspension of 6-[(2,2-diphenylethyl)amino]-9H-purine-2-carbonitrile (10.0 g, 0.03 mol) (see WO-A-00/23457) in 1,1,1-trichloroethane (250 ml). The suspension was heated to reflux. When all suspended solid had dissolved the reaction mixture was allowed to cool to room temperature and the solvent was removed under reduced pressure. The residue was twice dissolved in toluene (50 ml) and the solvent removed under reduced pressure. The residue was then dissolved in toluene (100 ml) and (2R,3R,4R,5S)-4,5-bis(acetyloxy)-2-[(acetyloxy)methyl]tetrahydro-3-furanyl acetate (10.3 g, 0.032 mol) was added. The solution was stirred at room temperature and trimethylsilyltrifluoromethanesulphonate (16 ml, 0.088 mol) was carefully added. The resulting solution was heated under reflux for 2 hours and then allowed to cool to room temperature. The reaction mixture was diluted by the addition of ethyl acetate (100 ml) and then washed with saturated aqueous sodium hydrogen carbonate (ten portions of 100 ml) and saturated aqueous sodium chloride solution (100 ml). The aqueous extracts were combined and washed with ethyl acetate (three portions of 100 ml). The combined organic layers were dried (anhydrous magnesium sulphate) and the solvent was removed under reduced pressure to give a solid that was purified by column chromatography on silica gel eluting with dichloromethane:methanol:0.88 concentrated aqueous ammonia (97:3:0.5 by volume gradually changing to 80:20:3 by volume) to give the title compound as a foam (8.5 g).

$^1$H-NMR (CDCl$_3$) δ: 7.95 (1H, s), 7.35–7.20 (10H, m), 6.15–6.10 (1H, m), 5.95–5.90 (1H, m), 5.80–5.75 (1H, m), 5.60–5.55 (1H, m), 4.45–4.35 (4H, m), 4.35–4.25 (2H, m), 2.15 (3H, s), 2.10 (3H, s), 2.05 (3H, s).

PREPARATION 19

(2R,3R,4S,5R)-2-{2-(Aminomethyl)-6-[(2,2-diphenylethyl)amino]-9H-purin-9-yl}-5-(hydroxymethyl)tetrahydro-3,4-furandiol

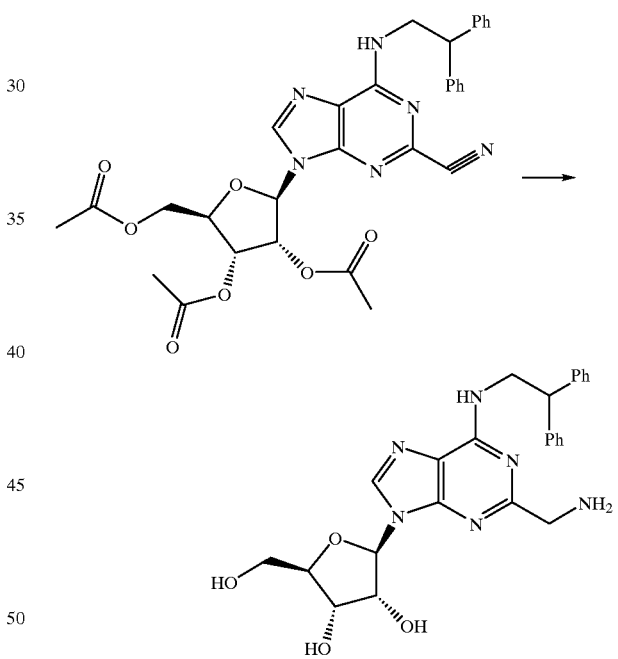

10% w/w Palladium on carbon (200 mg) was added to a solution of (2R,3R,4R,5R)-4-(acetyloxy)-2-[(acetyloxy)methyl]-5-{2-cyano-6-[(2,2-diphenylethyl)amino]-9H-purin-9-yl}tetrahydro-3-furanyl acetate (Preparation 18) (1.9 g, 3.2 mmol) in ethanol saturated with ammonia (100 ml). The reaction mixture was stirred under an atmosphere of hydrogen 414 kPa (60 psi) for 16 hours at room temperature. The solids were removed by filtration through Arbocel (Trade Mark) and the solvent was removed under reduced pressure. The residue was purified by column chromatography on silica gel eluting with dichloromethane:methanol:0.88 concentrated aqueous ammonia (90:10:1 by volume gradually changing to 80:20:2 by volume) to give the title compound as a solid (770 mg).

MS: 477 (MH+).

$^1$H-NMR (CDCl$_3$) δ: 8.10 (1H, s), 7.35–7.20 (8H, m), 5.90–5.85 (1H, m), 4.75–4.70 (1H, m), 4.50–4.40 (1H, m), 4.30–4.20 (2H, m), 4.10 (1H, m), 3.90–3.80 (2H, m), 3.70–3.65 (1 H, m).

PHARMACOLOGICAL ACTIVITY

All the compounds of Examples 1–4 were tested for anti-inflammatory activity by their ability to inhibit neutrophil function (which indicates A2a receptor agonist activity) by the method described on page 20 and all had an IC$_{50}$ of less than 1 micromolar.

What is claimed is:

1. A compound of the formula (I)

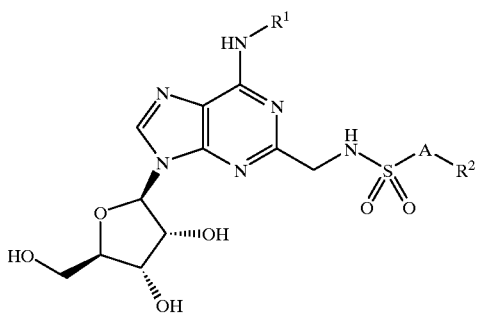

or a pharmaceutically acceptable salt or solvate thereof, wherein

R$^1$ is hydrogen or C$_1$–C$_6$ alkyl optionally substituted by 1 or 2 substituents each independently selected from phenyl and naphthyl, said phenyl and naphthyl being optionally substituted by C$_1$–C$_6$ alkyl, C$_1$–C$_6$ alkoxy, halo or cyano;

A is a bond or C$_1$–C$_3$ alkylene;

R$^2$ is (i) hydrogen, C$_1$–C$_6$ alkyl, C$_3$–C$_7$ cycloalkyl, phenyl or naphthyl, said C$_3$–C$_7$ cycloalkyl, phenyl or naphthyl being optionally substituted by C$_1$–C$_6$ alkyl, phenyl, C$_1$–C$_6$ alkoxy-(C$_1$–C$_6$)-alkyl, R$^3$R$^3$ N-(C$_1$–C$_6$)-alkyl, fluoro-(C$_1$–C$_6$)-alkyl, fluoro-(C$_1$–C$_6$)-alkoxy, C$_2$–C$_5$ alkanoyl, halo, —OR$^3$, cyano, —COOR$^3$, C$_3$–C$_7$ cycloalkyl, —S(O)$_m$R$^4$, —NR$^3$R$^3$, —SO$_2$NR$^3$R$^3$, —CONR$^3$R$^3$, —NR$^3$COR$^4$ or —NR$^3$SO$_2$R$^4$, with the proviso that R$^2$ is not hydrogen when A is a bond, or (ii) when A is C$_2$–C$_3$ alkylene, —NR$^7$R$^8$, —OR$^3$, —COOR$^3$, —OCOR$^4$, —SO$_2$R$^4$, —CN, —SO$_2$NR$^3$R$^3$, —NR$^3$COR$^4$ or —CONR$^3$R$^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, C$_1$–C$_6$ alkoxy-(C$_1$–C$_6$)-alkyl, R$^3$R$^3$N-(C$_1$–C$_6$)-alkyl, fluoro-(C$_1$–C$_6$)-alkyl, fluoro-(C$_1$–C$_6$)-alkoxy, fluoro-(C$_2$–C$_5$)-alkanoyl, halo, cyano, —OR$^5$, R$^6$, —COR$^5$, —NR$^5$R$^5$, —COOR$^5$, —S(O)$_m$R$^6$, —SO$_2$NR$^5$R$^5$, —CONR$^5$R$^5$, —NR$^5$SO$_2$R$^6$ or —NR$^5$COR$^6$ and optionally N-substituted by C$_1$–C$_6$ alkoxy-(C$_1$–C$_6$)-alkyl, R$^3$R$^3$N-(C$_2$–C$_6$)-alkyl, fluoro-(C$_1$–C$_6$)-alkyl, fluoro-(C$_2$–C$_5$)-alkanoyl, R$^6$, —COR$^5$, —COOR$^5$, —S(O)$_m$R$^6$, —SO$_2$NR$^5$R$^5$ or —CONR$^5$R$^5$;

R$^3$ is H, C$_1$–C$_6$ alkyl, C$_3$–C$_7$ cycloalkyl or phenyl;

R$^4$ is C$_1$–C$_6$ alkyl, C$_3$–C$_7$ cycloalkyl or phenyl;

R$^5$ is H, C$_1$–C$_6$ alkyl, C$_3$–C$_7$ cycloalkyl, phenyl, naphthyl or het;

R$^6$ is C$_1$–C$_6$ alkyl, C$_3$–C$_7$ cycloalkyl, phenyl, naphthyl or het;

either, R$^7$ and R$^8$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by C$_1$–C$_6$ alkyl, C$_3$–C$_8$ cycloalkyl, phenyl, C$_1$–C$_6$ alkoxy-(C$_1$–C$_6$)-alkyl, R$^3$R$^3$N-(C$_1$–C$_6$)-alkyl, fluoro-(C$_1$–C6)-alkyl, —CONR$^3$R$^3$, —COOR$^3$ or C$_2$–C$_5$ alkanoyl, and optionally substituted on a ring carbon atom not adjacent to a ring nitrogen atom by fluoro-(C$_1$–C$_6$)-alkoxy, halo, —OR$^3$, cyano, S(O)$_m$R$^4$, —NR$^3$R$^3$, —SO$_2$NR$^3$R$^3$, —NR$^3$COR$^4$ or —NR$^3$SO$_2$R$^4$, and said piperazin-1-yl and homopiperazin-1-yl being optionally substituted on the ring nitrogen atom not attached to A by C$_1$–C$_6$ alkyl, phenyl, C$_1$–C$_6$ alkoxy-(C$_2$–C$_6$)-alkyl, R$^3$R$^3$N-(C$_2$–C$_6$)-alkyl, fluoro-(C$_1$–C$_6$)-alkyl, C$_2$–C$_5$ alkanoyl, —COOR$^4$, C$_3$–C$_8$ cycloalkyl, —SO$_2$R$^4$, —SO$_2$NR$^3$R$^3$ or —CONR$^3$R$^3$ , or, R$^7$ is H, C$_1$–C$_6$ alkyl, C$_3$–C$_8$ cycloalkyl, phenyl or benzyl and R$^8$ H, C$_1$–C$_6$ alkyl, C$_3$–C$_8$ cycloalkyl, phenyl, benzyl, fluoro-(C$_1$–C$_6$)-alkyl, —CONR$^3$R$^3$, —COOR$^4$, C$_2$–C$_5$ alkanoyl or —SO$_2$NR$^3$R$^3$;

m is 0, 1 or 2; and

"het", used in the definitions of R$^5$ and R$^6$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by C$_1$–C$_6$ alkyl, C$_1$–C$_6$ alkoxy, cyano or halo.

2. A compound as claimed in claim 1 wherein

R$^1$ is hydrogen or C$_1$–C$_6$ alkyl optionally substituted by 1 or 2 substituents each independently selected from phenyl and naphthyl, said phenyl and naphthyl being optionally substituted by C$_1$–C$_6$ alkyl, C$_1$–C$_6$ alkoxy, halo or cyano;

A is a bond or C$_1$–C$_3$ alkylene;

R$^2$ is (i) hydrogen, C$_1$–C$_6$ alkyl, C$_3$–C$_7$ cycloalkyl, phenyl or naphthyl, said C$_3$–C$_7$ cycloalkyl, phenyl or naphthyl being optionally substituted by C$_1$–C$_6$ alkyl, phenyl, C$_1$–C$_6$ alkoxy-(C$_1$–C$_6$)-alkyl, amino-(C$_1$–C$_6$)-alkyl, fluoro-(C$_1$–C$_6$)-alkyl, fluoro-(C$_1$–C$_6$)-alkoxy, C$_2$–C$_5$ alkanoyl, halo, —OR$^3$, cyano, —COOR$^3$, C$_{3-C7}$ cycloalkyl, —S(O)$_m$R$^4$, —NR$^3$R$^3$, —SO$_2$NR$^3$R$^3$, —CONR$^3$R$^3$, —NR$^3$COR or —NR$^3$SO$_2$R$^4$, with the proviso that R$^2$ is not hydrogen when A is a bond, or (ii) when A is C$_2$–C$_3$ alkylene, —NR$^3$R$^3$, —OR$^3$, —COOR$^3$, —OCOR$^4$, —SO$_2$R$^4$, —CN, —SO$_2$NR$^3$R$^3$, —NR$^3$COR$^4$ or —CONR$^3$R$^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, C$_1$–C$_6$ alkoxy-(C$_1$–C$_6$)-alkyl, amino-(C$_1$–C$_6$)-alkyl, fluoro-(C$_1$–C$_6$)-alkyl, fluoro-(C$_1$–C$_6$)-alkoxy, fluoro-(C$_2$–C$_5$)-alkanoyl, halo, cyano, —OR$^5$, R$^6$, —COR$^5$, —NR$^5$R$^5$, —COOR$^5$, —S(O)$_m$R$^6$, —SO$_2$NR$^5$R$^5$, —CONR$^5$R$^5$, —NR$^5$SO$_2$R$^6$ or —NR$^5$COR$^6$ and optionally N-substituted by C$_1$–C$_6$ alkoxy-(C$_1$–C$_6$)-alkyl, amino-(C$_2$–C$_6$)-alkyl, fluoro-(C$_1$–C$_6$)-alkyl, fluoro-(C$_2$–C$_5$)-alkanoyl, R$^6$, —COR$^5$, —COOR$^5$, —S(O)$_m$R$^6$, —SO$_2$NR$^5$R$^5$ or —CONR$^5$R$^5$or (iv) when A is C$_2$–C$_3$ alkylene, N-linked azetidinyl, pyrrolidinyl, piperidinyl or piperazinyl, each being optionally C-substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$ —$NR^3R^3$, —$SO_2NR^3R^3$, —$CONR^3R^3$, —$NR^3COR^4$ or —$NR^3SO_2R^4$ and optionally N-substituted by $C_1$–$C_6$ alkyl, phenyl, $C_1$–$C_6$ alkoxy-($C_1$–$C_6$)-alkyl, amino-($C_2$–$C_6$)-alkyl, fluoro-($C_1$–$C_6$)-alkyl, $C_2$–$C_5$ alkanoyl, —$COOR^3$, $C_3$–$C_7$ cycloalkyl, —$S(O)_mR^4$ —$SO_2NR^3R^3$ or —$CONR^3R^3$;

$R^3$ is H, $C_1$–$C_6$ alkyl or phenyl;

$R^4$ is $C_1$–$C_6$ alkyl or phenyl;

$R^5$ is H, $C_1$–$C_6$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

m is 0, 1 or 2; and

"het", used in the definitions of $R^5$ and $R^6$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo.

3. A compound as claimed in claim 1 or claim 2 wherein A is a bond.

4. A compound as claimed in claim 1 or claim 2 wherein A is $C_1$–$C_3$ alkylene.

5. A compound as claimed in claim 1 wherein A is $C_2$–$C_3$ alkylene.

6. A compound as claimed in claim 5 wherein A is —$CH_2CH_2$—.

7. A compound as claimed in claim 2 wherein $R^2$ is $C_1$–$C_6$ alkyl or phenyl.

8. A compound as claimed in claim 7 wherein $R^2$ is 2-methylprop-1-yl or phenyl.

9. A compound as claimed in claim 6 wherein $R^2$ is —$NR^7R^8$.

10. A compound as claimed in claim 9 wherein $R^7$ is $C_1$–$C_6$ alkyl and $R^8$ is $C_3$–$C_8$ cycloalkyl.

11. A compound as claimed in claim 10 wherein $R^7$ is prop-2-yl and $R^8$ is cyclopentyl.

12. A compound as claimed in claim 2 wherein $R^1$ is $C_1$–$C_6$ alkyl substituted by 1 or 2 substituents each independently selected from phenyl and naphthyl.

13. A compound as claimed in claim 12 wherein $R^1$ is 2-phenylethyl, 2,2-diphenylethyl or 1-naphthylmethyl.

14. A compound as claimed in claim 1 wherein —A—$R^2$ is 2-[(2-propyl)(cyclopentyl)amino]ethyl, 2-methylprop-1-yl or phenyl.

15. A compound as claimed in claim 1 which is selected from the group consisting of:

N-({9-[(2R,3R,4S,5R)-3,4-dihydroxy-5-(hydroxymethyl) tetrahydro-2-furanyl]-6-[(2,2-diphenylethyl)amino]-9H-purin-2-yl}methyl)-2-methyl-1-propanesulfonamide;

N-{[9-[(2R,3R,4S,5R)-3,4-dihydroxy-5-(hydroxymethyl) tetrahydro-2-furanyl]-6-(phenethylamino)-9H-purin-2-yl]methyl}benzenesulfonamide;

N-({9-[(2R,3R,4S,5R)-3,4-dihydroxy-5-(hydroxymethyl) tetrahydro-2-furanyl]-6-[(1-naphthylmethyl)amino]-9H-purin-2-yl}methyl)benzenesulfonamide; and 2-[cyclopentyl(isopropyl)amino]-N-({9-[(2R,3R,4S,5R)-3,4-dihydroxy-5-(hydroxymethyl)tetrahydro-2-furanyl]-6-[(2,2-diphenylethyl)amino]-9H-purin-2-yl}methyl)ethanesulfonamide;

and the pharmaceutically acceptable salts and solvates thereof.

16. A pharmaceutical composition comprising a compound of the formula (I) or a pharmaceutically acceptable salt or solvate thereof, as claimed in claim 1, together with a pharmaceutically acceptable excipient, diluent or carrier.

17. A compound of the formula (I) or a pharmaceutically acceptable salt, solvate or composition thereof, as claimed in any one of claims 1 to 15 and 16, respectively, for use as a medicament.

18. The use of a compound of the formula (I) or a pharmaceutically acceptable salt, solvate or composition thereof, as claimed in any one of claims 1 to 15 and 16, respectively, for the manufacture of a medicament to treat a disease for which an A2a receptor agonist is indicated.

19. The use of a compound of the formula (I) or a pharmaceutically acceptable salt, solvate or composition thereof, as claimed in any one of claims 1 to 15 and 16, respectively, for the manufacture of an anti-inflammatory agent.

20. The use of a compound of the formula (I) or a pharmaceutically acceptable salt, solvate or composition thereof, as claimed in any one of claims 1 to 15 and 16, respectively, for the manufacture of a medicament for the treatment of a respiratory disease.

21. Use as claimed in claim 20 where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

22. The use of a compound of the formula (I) or a pharmaceutically acceptable salt, solvate or composition thereof, as claimed in any one of claims 1 to 15 and 16, respectively, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylon* gastritis, non-steroidal anti-inflammatory drug-induced damage to the gastro-intestinal tract or a psychotic disorder, or for wound healing.

23. A method of treatment of a mammal, including a human being, having a disease for which an A2a receptor agonist is indicated, comprising treating said mammal with an effective amount of a compound of the formula (I) or a pharmaceutically acceptable salt or solvate thereof as claimed in claim 1, or with a pharmaceutical composition containing said compound as claimed in claim 16.

24. A method of treatment of a mammal, including a human being, having an inflammatory disease, comprising treating said mammal with an effective amount of a compound of the formula (I) or a pharmaceutically acceptable salt or solvate thereof as claimed in claim 1, or with a pharmaceutical composition containing said compound as claimed in claim 16.

25. A method of treatment of a mammal, including a human being, having a respiratory disease, comprising treating said mammal with an effective amount of a compound of the formula (I) or a pharmaceutically acceptable salt or solvate thereof as claimed in claim 1, or with a pharmaceutical composition containing said compound as claimed in claim 16.

26. A method as claimed in claim 25 where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

27. A method of treatment of a mammal, including a human being, having septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohn's disease, inflammatory bowel disease, *Heliobacter pylori*-gastritis, non-*Heliobacter pylori*-gastritis, non-steroidal anti-inflammatory drug-induced damage to the gastrointestinal tract, a psychotic disorder, or in need of wound healing, comprising treating said mammal with an effective amount of a compound of the formula (I) or a pharmaceutically acceptable salt or solvate thereof as claimed in claim 1, or with a pharmaceutical composition containing said compound as claimed in claim 16.

28. A process for the preparation of a compound of the formula (I), as claimed in claim 1 or claim 2, or a pharmaceutically acceptable salt or solvate thereof, comprising the following Steps:

(a) deprotection of a compound of the formula (II):

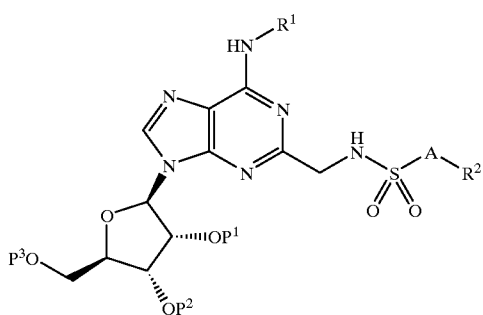

(II)

wherein $R^1$, $R^2$ and A are as defined in claim 1 or claim 2 and either (a) $P^1$, $P^2$ and $P^3$, when taken separately, are protecting groups, or (b) $P^1$ and $P^2$, when taken together are a protecting group and $P^3$ is a protecting group; the protecting groups in each case being removed either together or sequentially; or (b) deprotection of a compound of the formula (IIA):

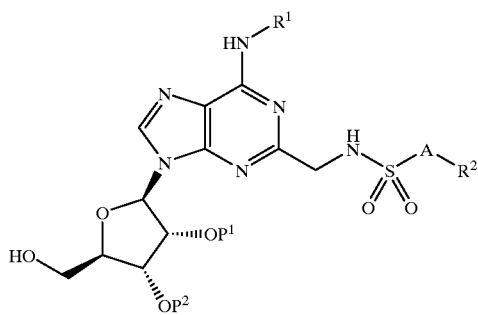

(IIA)

wherein $R^1$, $R^2$ and A are as defined in claim 1 or claim 2 and either (a) $P^1$ and $P^2$, when taken separately are protecting groups, or (b) $P^1$ and $P^2$, when taken together are a protecting group; protecting groups $P^1$ and $P^2$ when taken separately, being removed either together or sequentially; or (c) deprotection of a compound of the formula (IIB):

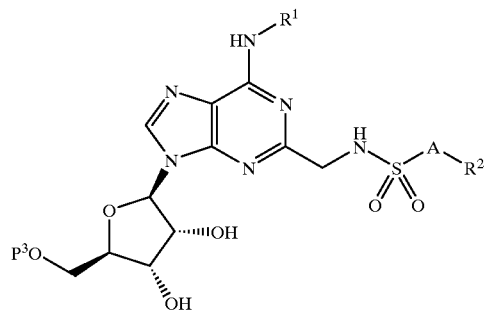

(IIB)

wherein $P^3$ is a protecting group and $R^1$, $R^2$ and A are as defined in claim 1 or claim 2; or (d) sulphonylation of a compound of the formula (XVIII):

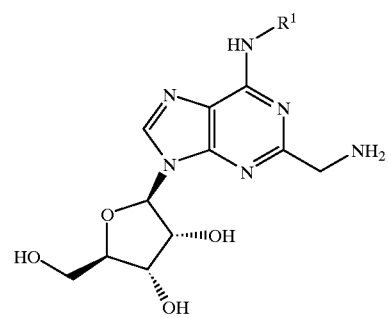

(XVIII)

wherein $R^1$ is as defined in claim 1 or claim 2, with a compound of the formula (VII):

$$R^2\text{—}A\text{—}SO_2\text{—}X \quad (VII)$$

wherein X is a leaving group and $R^2$ and A are as defined in claim 1 or claim 2;

any one of said Steps (a) to (d) being optionally followed by the conversion of a compound of the formula (I) to a pharmaceutically acceptable salt thereof.

29. A process for the preparation of a compound of the formula (I), as claimed in claim 1, in which A is —CH$_2$CH$_2$— and $R^2$ is —NR$^7$R$^8$, or a pharmaceutically acceptable salt or solvate thereof, comprising the reaction of a compound of the formula (XX):

(XX)

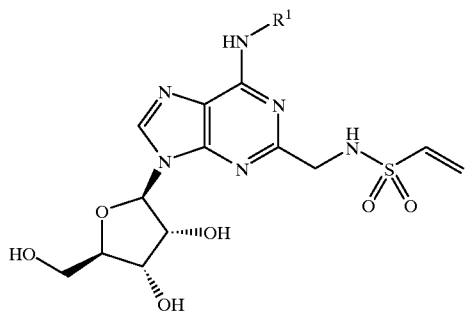

wherein R¹ is as defined in claim 1, with a compound of the formula (XXII):

R⁷R⁸NH   (XXII)

wherein R⁷ and R⁸ are as defined in claim 1;
said process being optionally followed by the conversion of a compound of the formula (I) to a pharmaceutically acceptable salt thereof.

30. A compound of the formula (II):

(II)

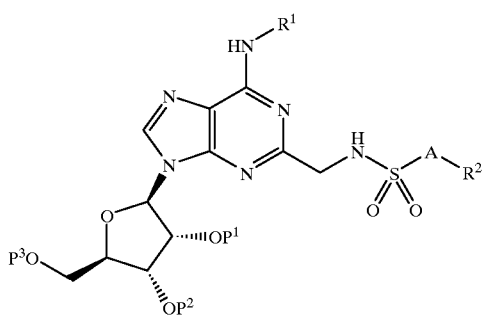

wherein either (a) P¹, P² and P³, when taken separately, are protecting groups, or (b) P¹ and P², when taken together are a protecting group and P³ is a protecting group; or
a compound of the formula (IIA):

(IIA)

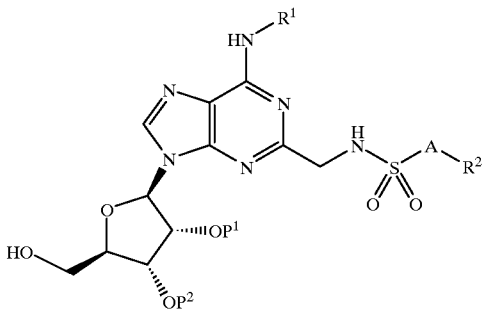

wherein either (a) P¹ and P², when taken separately, are protecting groups, or (b) P¹ and P², when taken together are a protecting group; or a compound of the formula (IIB):

(IIB)

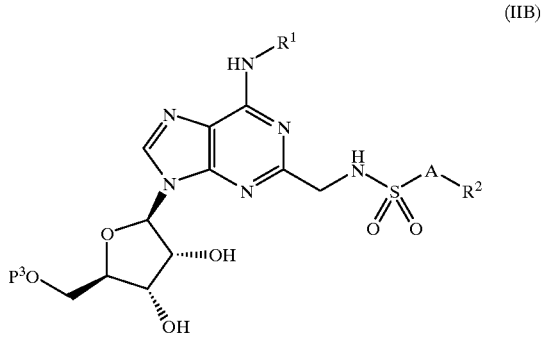

wherein P³ is a protecting group; or
a compound of the formula (IV), (V), (VI), or (XIV):

(IV)

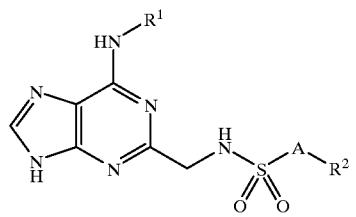

(V)

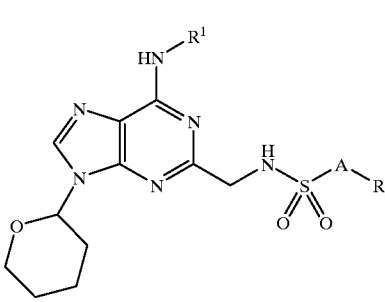

(VI)

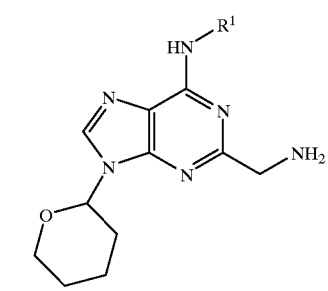

-continued

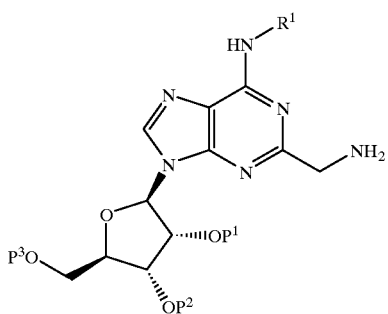

(XIV)

wherein either (a) $P^1$, $P^2$ and $P^3$, when taken separately, are protecting groups, or (b) $P^1$ and $P^2$, when taken together are a protecting group and $P^3$ is a protecting group; or a compound of the formula (XVI):

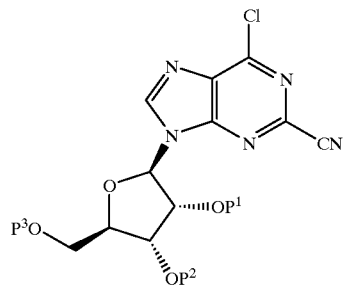

(XVI)

wherein either (a) $P^1$, $P^2$ and $P^3$, when taken separately, are protecting groups, or (b) $P^1$ and $P^2$, when taken together are a protecting group and $P^3$ is a protecting group; or a compound of the formula (XVIII):

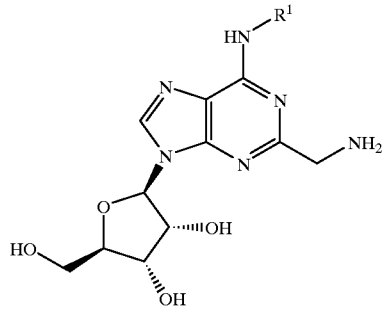

(XVIII)

wherein for the formulas (II), (IIA), (IIB), (IV), (V), (VI), (XIV), (XVI), and (XVIII) above, the groups $R^1$, $R^2$ and A are as defined in claim 1 or claim 2.

31. A compound of the formula (XV):

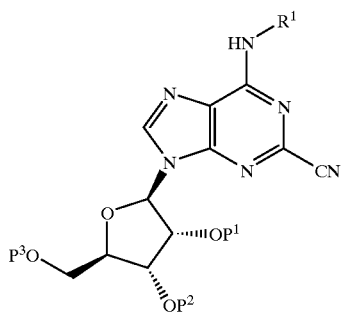

(XV)

wherein either (a) $P^1$, $P^2$ and $P^3$, when taken separately, are protecting groups, or (b) $P^1$ and $P^2$, when taken together are a protecting group and $P^3$ is a protecting group; or a compound of the formula (XIX):

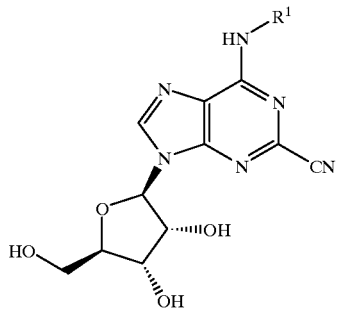

(XIX)

wherein for the formulas (XV) and (XIX) above, the group $R^1$ is defined as $C_1$–$C_6$ alkyl optionally substituted by 1 or 2 substituents each independently selected from the group consisting of phenyl and naphthyl, where said phenyl or naphthyl is optionally substituted by $C_1$–$C_6$ alkyl, $C_1$–$C_6$ alkoxy, halo or cyano.

32. A compound of the formula (XX):

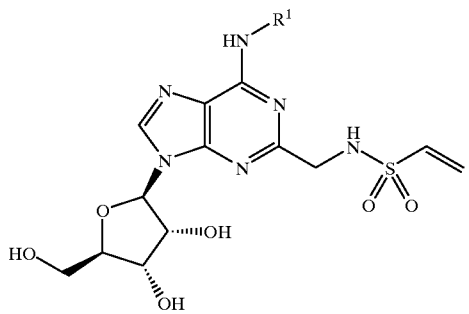

(XX)

wherein the group $R^1$ is as defined in claim 1.

* * * * *